(12) United States Patent
Liang

(10) Patent No.: US 10,851,084 B2
(45) Date of Patent: Dec. 1, 2020

(54) PIPERAZINE DERIVATIVES AS TRPML MODULATORS

(71) Applicant: CalyGene Biotechnology, Inc., Camden, DE (US)

(72) Inventor: Congxin Liang, Palm Beach Gardens, FL (US)

(73) Assignee: Lysoway Therapeutics, Inc., Cambridge, MA (US)

(*) Notice: Subject to any disclaimer, the term of this patent is extended or adjusted under 35 U.S.C. 154(b) by 0 days.

(21) Appl. No.: 16/311,272

(22) PCT Filed: Jun. 29, 2017

(86) PCT No.: PCT/US2017/039848
§ 371 (c)(1),
(2) Date: Dec. 19, 2018

(87) PCT Pub. No.: WO2018/005713
PCT Pub. Date: Jan. 4, 2018

(65) Prior Publication Data
US 2019/0248764 A1    Aug. 15, 2019

Related U.S. Application Data

(60) Provisional application No. 62/356,469, filed on Jun. 29, 2016.

(51) Int. Cl.
| | |
|---|---|
| *C07D 403/04* | (2006.01) |
| *C07D 401/04* | (2006.01) |
| *C07D 241/04* | (2006.01) |
| *C07D 295/096* | (2006.01) |
| *C07D 213/76* | (2006.01) |
| *C07D 295/135* | (2006.01) |
| *C07D 239/48* | (2006.01) |
| *A61P 21/00* | (2006.01) |
| *A61P 17/00* | (2006.01) |
| *A61P 25/16* | (2006.01) |
| *A61P 25/28* | (2006.01) |

(52) U.S. Cl.
CPC ........... *C07D 403/04* (2013.01); *A61P 17/00* (2018.01); *A61P 21/00* (2018.01); *A61P 25/16* (2018.01); *A61P 25/28* (2018.01); *C07D 213/76* (2013.01); *C07D 239/48* (2013.01); *C07D 241/04* (2013.01); *C07D 295/096* (2013.01); *C07D 295/135* (2013.01); *C07D 401/04* (2013.01)

(58) Field of Classification Search
CPC ......... A61P 17/00; A61P 21/00; A61P 25/16; A61P 25/28; C07D 213/76; C07D 239/48; C07D 241/04; C07D 295/096; C07D 295/135; C07D 401/04; C07D 403/04

See application file for complete search history.

(56) References Cited

U.S. PATENT DOCUMENTS 6,403,607 B1 * 6/2002 Hidaka ................ C07C 311/08
514/231.2

FOREIGN PATENT DOCUMENTS

| WO | 2006/111560 A1 | 10/2006 |
|---|---|---|
| WO | 2018/208630 A1 | 11/2018 |

OTHER PUBLICATIONS

Youdim, The Path from Anti Parkinson Drug Selegiline and Rasagiline to Multifunctional Neuroprotective Anti Alzheimer Drugs Ladostigil and M30, Current Alzheimer Research, 3, 541-550 (2006). (Year: 2006).*
Shen et al. "Lipid storage disorders block lysosomal trafficking by inhibiting a TRP channel and lysosomal calcium release", Nat. Commun., 3, 731, 2012.
Grimm et al., "Small Molecule Activators of TRPML3", Chem. Biol., 17(2), 135-148, 2010.
Grimm et al., "Constitutive activity of TRPML2 and TRPML3 channels versus activation by low extracellular sodium and small molecules.", J. Biol. Chem., 287(27), 22701-22708, 2012.
Chen et al., "A small molecule restores function to TRPML1 mutant isoforms responsible for mucolipidosis type IV.", Nat. Commun. 5, 4681, 2014.
Feng et al., "Differential mechanisms of action of the mucolipin synthetic agonist, ML-SA1, on insect TRPML and mammalian TRPML1.", Cell Calcium. 56(6), 446-456, 2014.
Wang et al., "Up-regulation of lysosomal TRPML1 channels is essential for lysosomal adaptation to nutrient starvation", Proc Natl Acad Sci U S A. , 112(11), E1373-E1381, 2015.
Li et al., "Regulation of membrane trafficking by signalling on endosomal and lysosomal membranes", J. Physiol., 591 (18), 4389-4401, 2013.

* cited by examiner

*Primary Examiner* — Erich A Leeser
(74) *Attorney, Agent, or Firm* — Milstein Zhang & Wu LLC

(57) ABSTRACT

The new piperazine derivatives are modulators of TRPML and are useful in treating disorders related to TRPML activities such as lysosome storage diseases, muscular dystrophy, age-related common neurodegenerative diseases, oxidative stress or reactive oxygen species (ROS) related diseases, and ageing.

18 Claims, 3 Drawing Sheets

PIPERAZINE DERIVATIVES AS TRPML MODULATORS

CROSS-REFERENCE TO RELATED APPLICATIONS

This application claims the priority of U.S. provisional application Ser. No. 62/356,469, filed Jun. 29, 2016, which is incorporated herein by reference in its entirety.

TECHNICAL FIELD OF THE INVENTION

This invention relates to novel piperazine derivatives, their salts, solvates, hydrates and polymorphs thereof as TRPML modulators. The invention also provides compositions comprising a compound of this invention and the use of such compositions in methods of treating diseases and conditions associated with TRPML and are useful in treating disorders related to TRPML activities such as lysosome storage diseases, muscular dystrophy, age-related common neurodegenerative diseases, reactive oxygen species (ROS) or oxidative stress related diseases, and ageing.

BACKGROUND OF THE INVENTION

The lysosome, the cell's recycling center, can mediate the degradation of a variety of biomaterials (proteins, lipids, and membranes) into smaller molecules or building blocks, which will be subsequently transported out of lysosomes for reutilization or energy [see e.g. de Duve, C., The lysosome turns fifty. Nat Cell Biol, 2005. 7(9): p. 847-9. Parkinson-Lawrence, E. J., et al., Lysosomal storage disease: revealing lysosomal function and physiology. Physiology (Bethesda), 2010. 25(2): p. 102-15]. Problems in either the degradation step (due to lack of hydrolytic enzymes) or the transport step lead to lysosome storage (of accumulated materials) and more than 50 human diseases collectively called lysosome storage diseases (LSDs). Interestingly, lysosome storage can in turn affect lysosomal degradation and membrane transport/trafficking, making a positive feedback loop and a vicious cycle. Because lysosome storage is also seen in common neurodegenerative diseases such as Alzheimer's and Parkinson's, understanding the mechanisms underlying the positive feedback loop may provide therapeutic approaches not only for LSDs, but also for common sporadic neurodegenerative diseases. A lysosome-localized $Ca^{2+}$ channel, TRPML1, has been recently identified as a key regulator of most membrane trafficking processes in the lysosome. Human mutations of TRPML1 cause lysosomal trafficking defects, lysosome storage, and neurodegenerative diseases.

TRPML1 (abbreviated as ML1), a member of the TRP-type $Ca^{2+}$ channel superfamily, is the principle $Ca^{2+}$ channel in the lysosome [see e.g. Cheng, X., et al., Mucolipins: Intracellular TRPML1-3 channels. FEBS Lett, 2010. 584 (10): p. 2013-21]. Loss-of-function mutations in the human TRPML1 gene cause Type IV Mucolipidosis (ML4), a lysosome storage neurodegenerative disease. TRPML1 (abbreviated as $ML1^{-/-}$) skin fibroblasts from ML4 patients are characterized by the accumulation of enlarged endosomal/lysosomal compartments (vacuoles) in which lipids and other biomaterials build up, suggestive of trafficking defects. Analyses of trafficking kinetics suggest that the primary defects are in the late endocytic pathways. First, ML1 is likely to be required for the formation of transport vesicles from the LEL to the Trans-Golgi Network (TGN) (LEL-to-TGN retrograde trafficking). Second, fusion of lysosomes with the plasma membrane (referred to as lysosomal exocytosis), a process that is important in cellular waste elimination, membrane repair, and phagocytosis, is defective in ML4 cells. Defects in either trafficking steps could lead to lysosome storage. Because the release of $Ca^{2+}$ from lysosomes (lysosomal $Ca^{2+}$ release) is essential for both trafficking steps, it is hypothesize that ML1 is indeed the $Ca^{2+}$ release channel that regulates lysosomal trafficking.

$PI(3,5)P_2$ is a low-abundance phosphoinositide, is the primary activator of ML1, and a positive regulator of lysosomal trafficking. Both TRPML-lacking and $PI(3,5)P_2$-deficient cells exhibit defects in LEL-to-Golgi retrograde trafficking and autophagosome-lysosome fusion, suggesting that the TRPML1-$PI(3,5)P_2$ system represents a common signaling pathway essential for late endocytic trafficking.

Due to the function of lysosome in lysosomal trafficking, lysosomes are required for quality-control regulation of mitochondria, the "power house" of the cell and the major source of endogenous ROS (reactive oxygen species). Damaged mitochondria causes oxidative stress, which is a common feature of most LSDs, common neurodegenerative diseases, and ageing (Xu, H, and Ren, D. Lysosomal physiology. Annual review of physiology 2015, 77, 57-80). Recent studies suggest that mitochondria are localized in close physical proximity to lysosomes (Elbaz-Alon et al. A dynamic interface between vacuoles and mitochondria in yeast. Dev Cell 2014, 30, 95-102. Li et al. ROS and Autophagy: Interactions and Molecular Regulatory Mechanisms. Cell Mol Neurobiol 2015, 35, 615-621). Hence the lysosomal membrane is potentially an accessible and direct target of ROS signaling. Given that ROS reportedly regulate ion channels (Bogeski, I., and Niemeyer, B. A. Redox regulation of ion channels. Antioxid Redox Signal 2014, 21, 859-862), it is possible that lysosomal conductances, particularly through lysosomal $Ca^{2+}$ channels such as TRPML1, may mediate ROS-regulation of lysosomal function. Indeed, electrophysiological studies revealed that whole-endolysosome TRPML1 currents were directly activated by ROS.

A regulatory imbalance can result in elevated ROS levels and oxidative stress, which are believed to underlie a variety of metabolic and neurodegenerative diseases, as well as ageing (Barnham et al. Neurodegenerative diseases and oxidative stress. Nat Rev Drug Discov 2004, 3, 205-214; Scherz-Shouval, R., and Elazar, Z. Regulation of autophagy by ROS: physiology and pathology. Trends Biochem Sci 2011, 36, 30-38). Given the role of TRPML1 in mediating ROS-induced autophagy, a TRPML1 agonist might be able to clear the excessive ROS, thereby ameliorating the ROS related diseases and ageing, especially photo ageing in the skin.

Transcription factor (TF)EB regulates autophagy and lysosome biogenesis. Overexpression of TFEB has been reportedly induce cellular clearance in a number of lysosome storage diseases, including Pombe Disease, Cystinosis, multiple sulfatase deficiency, as well as common neurodegenerative diseases, including Parkinson's disease and Huntinton's disease (Settembre, C., et al., Signals from the lysosome: a control centre for cellular clearance and energy metabolism. Nat Rev Mol Cell Biol, 2013. 14(5): p. 283-96). Therefore, activation of TRPML1 by TRPML1 agonists may also lead to cellular clearance in all the aforementioned diseases, providing therapeutic targets for these devastating diseases.

Recently, a potent synthetic agonist for TRPML1 has been reported [Shen, D., et al., Lipid storage disorders block lysosomal trafficking by inhibiting a TRP channel and lysosomal calcium release. Nat Commun, 2012. 3: p. 731]. This SF-51-related compound (Mucolipin Synthetic Agonist 1 or ML-SA1) that could induce significant $[Ca2+]_{cyt}$ increases in HEK293 cells stably or transiently expressing ML1-4A. In electrophysiological assays, ML-SA1 robustly activated whole-cell $I_{ML1-4A}$ and whole-endolysosome $I_{ML1}$. ML-SA1 also activated whole-cell $I_{TRPML2}$ and $I_{TRPML3}$, but not six other related channels. ML-SA1 (10 μM) activation of whole-endolysosome $I_{ML1}$ was comparable to the effect of the endogenous TRPML agonist PI(3,5)P2 (1 μM), and these agonists were synergistic with each other. ML-SA1 activated an endogenous whole-endolysosome TRPML-like current ($I_{ML-L}$) in all mammalian cell types that were investigated, including Chinese Hamster Ovary (CHO), Cos-1, HEK293, skeletal muscle, pancreatic β and macrophage cells. ML-SA1 activated whole-endolysosome $I_{ML-L}$ in wild-type (WT; ML1$^{+/+}$), but not ML4 (ML1$^{-/-}$) human fibroblasts, suggesting that although ML-SA1 targets all three TRPMLs, the expression levels of TRPML2 and TRPML3 are very low, and TRPML1 is the predominant lysosomal TRPML channel in this cell type. These results suggest that ML-SA1 is a reasonably specific and potent agonist that can be a useful for modulating the functions of TRPMLs. (FIG. 1)

High concentrations of ML-SA1 (~10 μM) are needed to effectively activate TRPMLs. Since that concentration is usually difficult to achieve in vivo, ML-SA1 cannot be used to treat the above TRPML related diseases. Herein we report a new class of compounds as more potent TRPML activators. These compounds might be useful in treating disorders related to TRPML activities such as lysosome storage diseases, muscular dystrophy, age-related common neurodegenerative diseases, ROS or oxidative stress related diseases, and ageing.

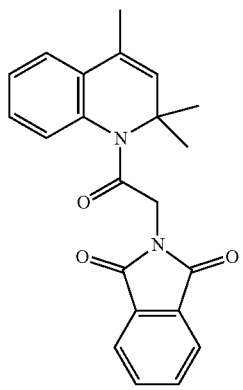

SF-51

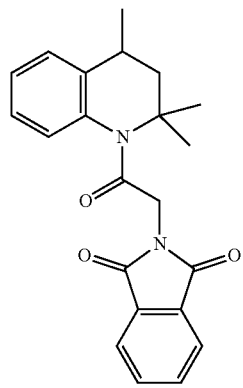

ML-SA1

SUMMARY OF THE INVENTION

The invention relates to piperazine containing compounds, compositions comprising the compounds, and methods of using the compounds and compound compositions. The compounds and compositions comprising them are useful for treating or preventing disease or disease symptoms mediated by or associated with TRPMLs.

In one aspect, the invention provides a TRPML modulatory compound of Formula I,

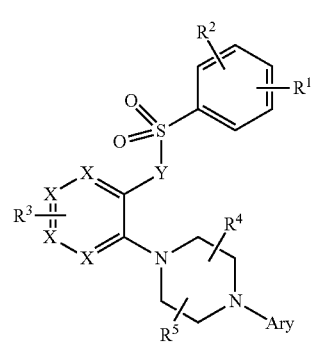

I or a salt thereof; or a prodrug, or a salt of a prodrug thereof; or a hydrate, solvate, or polymorph thereof; wherein:

each X is independently $CR_6$ or N;

Y is $NR_7$ or $CR_8R_9$;

Ary is phenyl or heteroaryl optionally substituted with 1, 2, or 3 substituents independently selected from $C_{1-3}$ alkyl, halo, OH, CN, OR, NHR, NRR', N(R)C(=O)R', N(R)C(=O)(O)R', OC(=O)NRR', C(=O)R, C(=O)NRR', N(R)S(O)2R', S(O)2R, and S(O)2NRR';

$R_1$, $R_2$, $R_3$, $R_4$, $R_5$, $R_6$, $R_7$, $R_8$, $R_9$ each are independently H, $C_{1-3}$ alkyl, halogen, oxo, OH, CN, OR, NHR, NRR', N(R)C(=O)R', N(R)C(=O)(O)R', OC(=O)NRR', C(=O)R, C(=O)NRR', N(R)S(O)2R', S(O)2R, and S(O)2NRR';

R, R' are independently H, $C_{1-3}$ alkyl.

In another aspect, the compounds of this invention, and compositions comprising them, are useful for treating or lessening the severity of TRPMLs modulated diseases, disorders, or symptoms thereof.

In another aspect, the invention relates to a method of treating a disease or disease symptom in a subject in need thereof including administering to the subject an effective amount of a compound of any formulae herein, or pharmaceutical salt, solvate or hydrate thereof (or composition thereof). The disease or disease symptom can be any of those modulated by TRPMLs. The disease or disease symptom can be, for example, lysosome storage diseases (e.g., including those delineated herein), ROS or oxidative stress related diseases, and ageing.

DETAILED DESCRIPTION OF THE INVENTION

Definitions

Figure 1:
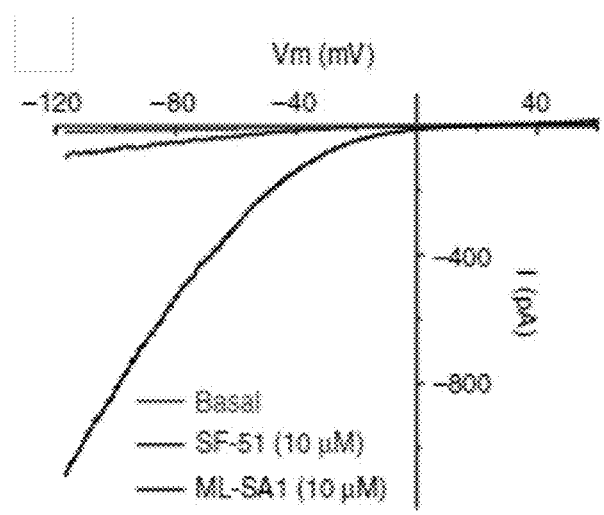
FIG. 1 shows certain experimental data of SF-51 and ML-SA1.

The terms "ameliorate" and "treat" are used interchangeably and both mean decrease, suppress, attenuate, diminish, arrest, or stabilize the development or progression of a disease (e.g., a disease or disorder delineated herein).

By "disease" is meant any condition or disorder that damages or interferes with the normal function of a cell, tissue, or organ.

By "marker" is meant any alteration that is associated with a disease or disorder. For example, any protein or polynucleotide having an alteration in expression level or activity that is associated with a disease or disorder.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The term "compound" as used herein, is also intended to include salts, prodrugs, and prodrug salts of a compound of formulae herein. The term also includes any solvates, hydrates, and polymorphs of any of the foregoing. The specific recitation of "prodrug," "prodrug salt," "solvate," "hydrate," or "polymorph" in certain aspects of the invention described in this application shall not be interpreted as an intended omission of these forms in other aspects of the invention where the term "compound" is used without recitation of these other forms.

A salt of a compound of this invention is formed between an acid and a basic group of the compound, such as an amino functional group, or a base and an acidic group of the compound, such as a carboxyl functional group. According to another preferred embodiment, the compound is a pharmaceutically acceptable acid addition salt.

As used herein and unless otherwise indicated, the term "prodrug" means a derivative of a compound that can hydrolyze, oxidize, or otherwise react under biological conditions (in vitro or in vivo) to provide a compound of this invention. Prodrugs may only become active upon such reaction under biological conditions, or they may have activity in their unreacted forms. Examples of prodrugs contemplated in this invention include, but are not limited to, analogs or derivatives of compounds of any one of the formulae disclosed herein that comprise biohydrolyzable moieties such as amides, esters, carbamates, carbonates, and phosphate analogues. Prodrugs can typically be prepared using well-known methods, such as those described by Burger's Medicinal Chemistry and Drug Discovery (1995) 172-178, 949-982 (Manfred E. Wolff ed., 5th ed); see also Goodman and Gilman's, The Pharmacological basis of Therapeutics, 8th ed., McGraw-Hill, Int. Ed. 1992, "Biotransformation of Drugs".

As used herein and unless otherwise indicated, the term "biohydrolyzable moiety" means a functional group (e.g., amide, ester, carbamate, carbonate, or phosphate analogue, that either: 1) does not destroy the biological activity of the compound and confers upon that compound advantageous properties in vivo, such as uptake, duration of action, or onset of action; or 2) is itself biologically inactive but is converted in vivo to a biologically active compound.

A prodrug salt is a compound formed between an acid and a basic group of the prodrug, such as an amino functional group, or a base and an acidic group of the prodrug, such as a carboxyl functional group. In a one embodiment, the prodrug salt is a pharmaceutically acceptable salt.

Particularly favored prodrugs and prodrug salts are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or central nervous system) relative to the parent species. Preferred prodrugs include derivatives where a group that enhances aqueous solubility or active transport through the gut membrane is appended to the structure of formulae described herein. See, e.g., Alexander, J. et al. Journal of Medicinal Chemistry 1988, 31, 318-322; Bundgaard, H. Design of Prodrugs; Elsevier: Amsterdam, 1985; pp 1-92; Bundgaard, H.; Nielsen, N. M. Journal of Medicinal Chemistry 1987, 30, 451-454; Bundgaard, H. A Textbook of Drug Design and Development; Harwood Academic Publ.: Switzerland, 1991; pp 113-191; Digenis, G. A. et al. Handbook of Experimental Pharmacology 1975, 28, 86-112; Friis, G. J.; Bundgaard, H. A Textbook of Drug Design and Development; 2 ed.; Overseas Publ.: Amsterdam, 1996; pp 351-385; Pitman, I. H. Medicinal Research Reviews 1981, 1, 189-214.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound or a prodrug of a compound of this invention.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylenesulfonate, phenylacetate, phenylpropionate, phenylbutyrate, citrate, lactate, -hydroxybutyrate, glycolate, maleate, tartrate, methanesulfonate, propanesulfonate, naphthalene-1-sulfonate, naphthalene-2-sulfonate, mandelate and the like salts. Preferred pharmaceutically acceptable acid addition salts include those formed with mineral acids such as hydrochloric acid and hydrobromic acid, and especially those formed with organic acids such as maleic acid.

Suitable bases for forming pharmaceutically acceptable salts with acidic functional groups of prodrugs of this invention include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N, N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

As used herein, the term "hydrate" means a compound which further includes a stoichiometric or non-stoichiometric amount of water bound by non-covalent intermolecular forces.

As used herein, the term "solvate" means a compound which further includes a stoichiometric or non-stoichiometric amount of solvent such as water, acetone, ethanol, methanol, dichloromethane, 2-propanol, or the like, bound by non-covalent intermolecular forces.

As used herein, the term "polymorph" means solid crystalline forms of a compound or complex thereof which may be characterized by physical means such as, for instance, X-ray powder diffraction patterns or infrared spectroscopy. Different polymorphs of the same compound can exhibit different physical, chemical and/or spectroscopic properties. Different physical properties include, but are not limited to stability (e.g., to heat, light or moisture), compressibility and density (important in formulation and product manufacturing), hygroscopicity, solubility, and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

The term "substantially free of other stereoisomers" as used herein means less than 25% of other stereoisomers, preferably less than 10% of other stereoisomers, more preferably less than 5% of other stereoisomers and most preferably less than 2% of other stereoisomers, or less than "X" % of other stereoisomers (wherein X is a number between 0 and 100, inclusive) are present. Methods of obtaining or synthesizing diastereomers are well known in the art and may be applied as practicable to final compounds or to starting material or intermediates. Other embodiments are those wherein the compound is an isolated compound. The term "at least X % enantiomerically enriched" as used herein means that at least X % of the compound is a single enantiomeric form, wherein X is a number between 0 and 100, inclusive.

The term "stable compounds", as used herein, refers to compounds which possess stability sufficient to allow manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"Stereoisomer" refers to both enantiomers and diastereomers.

As used herein, the term "halo" or "halogen" refers to any radical of fluorine, chlorine, bromine or iodine.

The terms "alk" or "alkyl" refer to straight or branched chain hydrocarbon groups having 1 to 12 carbon atoms, preferably 1 to 8 carbon atoms. The expression "lower alkyl" refers to alkyl groups of 1 to 4 carbon atoms (inclusive).

The term "arylalkyl" refers to a moiety in which an alkyl hydrogen atom is replaced by an aryl group.

The term "alkenyl" refers to straight or branched chain hydrocarbon groups of 2 to 10, preferably 2 to 4, carbon atoms having at least one double bond. Where an alkenyl group is bonded to a nitrogen atom, it is preferred that such group not be bonded directly through a carbon bearing a double bond.

The term "alkoxy" refers to an —O-alkyl radical. The term "alkylenedioxo" refers to a divalent species of the structure —O—R—O—, in which R represents an alkylene.

The term "alkynyl" refers to straight or branched chain hydrocarbon groups of 2 to 10, preferably 2 to 4, carbon atoms having at least one triple bond. Where an alkynyl group is bonded to a nitrogen atom, it is preferred that such group not be bonded directly through a carbon bearing a triple bond.

The term "alkylene" refers to a divalent straight chain bridge of 1 to 5 carbon atoms connected by single bonds (e.g., —(CH$_2$)$_x$—, wherein x is 1 to 5), which may be substituted with 1 to 3 lower alkyl groups.

The term "alkenylene" refers to a straight chain bridge of 2 to 5 carbon atoms having one or two double bonds that is connected by single bonds and may be substituted with 1 to 3 lower alkyl groups. Exemplary alkenylene groups are —CH=CH—CH=CH—, —CH$_2$—CH=CH—, —CH$_2$—CH=CH—CH$_2$—, —C(CH$_3$)$_2$CH=CH— and —CH(C$_2$H$_5$)—CH=CH—.

The term "alkynylene" refers to a straight chain bridge of 2 to 5 carbon atoms that has a triple bond therein, is connected by single bonds, and may be substituted with 1 to 3 lower alkyl groups. Exemplary alkynylene groups are —C≡C—, —CH$_2$—C≡C—, —CH(CH$_3$)C≡C— and —C≡C—CH(C$_2$H$_5$)CH$_2$—.

The terms "cycloalkyl" and "cycloalkenyl" as employed herein includes saturated and partially unsaturated cyclic, respectively, hydrocarbon groups having 3 to 12 carbons, preferably 3 to 8 carbons, and more preferably 3 to 6 carbon.

The terms "Ar" or "aryl" refer to aromatic cyclic groups (for example 6 membered monocyclic, 10 membered bicyclic or 14 membered tricyclic ring systems) which contain 6 to 14 carbon atoms. Exemplary aryl groups include phenyl, naphthyl, biphenyl and anthracene.

"Heteroaryl" refers to a monocyclic or fused ring (i.e., rings which share an adjacent pair of atoms) group of 5 to 12 ring atoms containing one, two, three or four ring heteroatoms selected from N, O, or S, the remaining ring atoms being C, and, in addition, having a completely conjugated pi-electron system, wherein 0, 1, 2, 3, or 4 atoms of each ring may be substituted by a substituent. Examples, without limitation, of heteroaryl groups are pyrrole, furan, thiophene, imidazole, oxazole, thiazole, pyrazole, pyridine, pyrimidine, quinoline, quinazoline, isoquinoline, purine and carbazole.

The terms "heterocycle", "heterocyclic" or "heterocyclo" refer to fully saturated or partially unsaturated cyclic groups, for example, 3 to 7 membered monocyclic, 7 to 12 membered bicyclic, or 10 to 15 membered tricyclic ring systems, which have at least one heteroatom in at least one ring, wherein 0, 1, 2 or 3 atoms of each ring may be substituted by a substituent. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system.

The term "heterocyclyl" refers to fully saturated or partially unsaturated cyclic groups, for example, 3 to 7 membered monocyclic, 7 to 12 membered bicyclic, or 10 to 15 membered tricyclic ring systems, which have at least one heteroatom in at least one ring, wherein 0, 1, 2 or 3 atoms of each ring may be substituted by a substituent. Each ring of the heterocyclyl group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclyl group may be attached at any heteroatom or carbon atom of the ring or ring system.

The term "substituents" refers to a group "substituted" on any functional group delineated herein, e.g., alkyl, alkenyl, alkynyl, cycloalkyl, cycloalkenyl, aryl, heterocyclyl, or heteroaryl group at any atom of that group. Suitable substituents include, without limitation halogen, CN, $NO_2$, $OR^{15}$, $SR^{15}$, $S(O)_2OR^{15}$, $NR^{15}R^{16}$, $C_1$-$C_2$ perfluoroalkyl, $C_1$-$C_2$ perfluoroalkoxy, 1,2-methylenedioxy, $C(O)OR^{15}$, $C(O)NR^{15}R^{16}$, $OC(O)NR^{15}R^{16}$, $NR^{15}C(O)NR^{15}R^{16}$, $C(NR^{16})NR^{15}R^{16}$, $NR^{15}C(NR^{16})NR^{15}R^{16}$, $S(O)_2NR^{15}R^{16}$, $R^{17}$, $C(O)R^{17}$, $NR^{15}C(O)R^{17}$, $S(O)R^{17}$, $S(O)_2R^{17}$, $R^{16}$, oxo, $C(O)R^{16}$, $C(O)(CH_2)nOH$, $(CH_2)nOR^{15}$, $(CH_2)nC(O)NR^{15}R^{16}$, $NR^{15}S(O)_2R^{17}$, where n is independently 0-6 inclusive. Each R is independently hydrogen, $C_1$-$C_4$ alkyl or $C_3$-$C_6$ cycloalkyl. Each $R^{16}$ is independently hydrogen, alkenyl, alkynyl, $C_3$-$C_6$ cycloalkyl, aryl, heterocyclyl, heteroaryl, $C_3$-$C_4$ alkyl or $C_1$-$C_4$ alkyl substituted with $C_3$-$C_6$ cycloalkyl, aryl, heterocyclyl or heteroaryl. Each $R^{17}$ is independently $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl. Each $C_3$-$C_6$ cycloalkyl, aryl, heterocyclyl, heteroaryl and $C_1$-$C_4$ alkyl in each $R^{15}$, $R^{16}$ and $R^{17}$ can optionally be substituted with halogen, CN, $C_1$-$C_4$ alkyl, OH, $C_1$-$C_4$ alkoxy, $NH_2$, $C_1$-$C_4$ alkylamino, $C_1$-$C_4$ dialkylamino, $C_1$-$C_2$ perfluoroalkyl, $C_1$-$C_2$ perfluoroalkoxy, or 1,2-methylenedioxy.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also be represented in multiple tautomeric forms, in such instances, the invention expressly includes all tautomeric forms of the compounds described herein. All such isomeric forms of such compounds are expressly included in the present invention. All crystal forms of the compounds described herein are expressly included in the present invention.

Compounds of the Invention

In one aspect, the present invention provides a compound of Formula I:

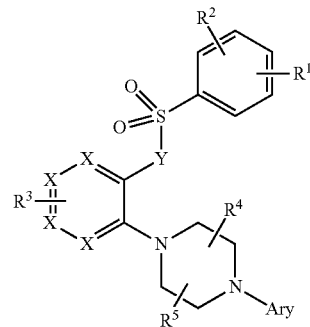

or a salt thereof; or a prodrug, or a salt of a prodrug thereof; or a hydrate, solvate, or polymorph thereof; wherein:

each X is independently $CR_6$ or N;

Y is $NR_7$ or $CR_8R_9$;

Ary is phenyl or heteroaryl optionally substituted with 1, 2, or 3 substituents independently selected from $C_{1-3}$ alkyl, halo, OH, CN, OR, NHR, NRR', $N(R)C(=O)R'$, $N(R)C(=O)(O)R'$, $OC(=O)NRR'$, $C(=O)R$, $C(=O)NRR'$, $N(R)S(O)2R'$, $S(O)2R$, and $S(O)2NRR'$;

$R_1$, $R_2$, $R_3$, $R_4$, $R_5$, $R_6$, $R_7$, $R_8$, $R_9$ each are independently H, $C_{1-3}$ alkyl, halogen, oxo, OH, CN, OR, NHR, NRR', $N(R)C(=O)R'$, $N(R)C(=O)(O)R'$, $OC(=O)NRR'$, $C(=O)R$, $C(=O)NRR'$, $N(R)S(O)2R'$, $S(O)2R$, and $S(O)2NRR'$;

R, R' are independently H, $C_{1-3}$ alkyl.

In one embodiment, the invention provides a compound of Formula I wherein Y is $NR_7$.

In another embodiment, the invention provides a compound of Formula I wherein Y is $CR_8R_9$.

In a further embodiment, the invention provides a compound of Formula I wherein all X is $CR_6$ and each $R_6$ is independently selected from H, $C_{1-3}$ alkyl, halogen.

Representative compounds of the invention are depicted in Table 1. In these examples the stereochemistry at the chiral carbon atoms is independently either RS, R, or S, unless specified. The structures depicted herein, including the Table 1 structures, may contain certain —NH—, —$NH_2$ (amino) and —OH (hydroxyl) groups where the corresponding hydrogen atom(s) do not explicitly appear; however they are to be read as —NH—, —NH$_2$ or —OH as the case may be. In certain structures, a stick bond is drawn and is meant to depict a methyl group.
TABLE 1
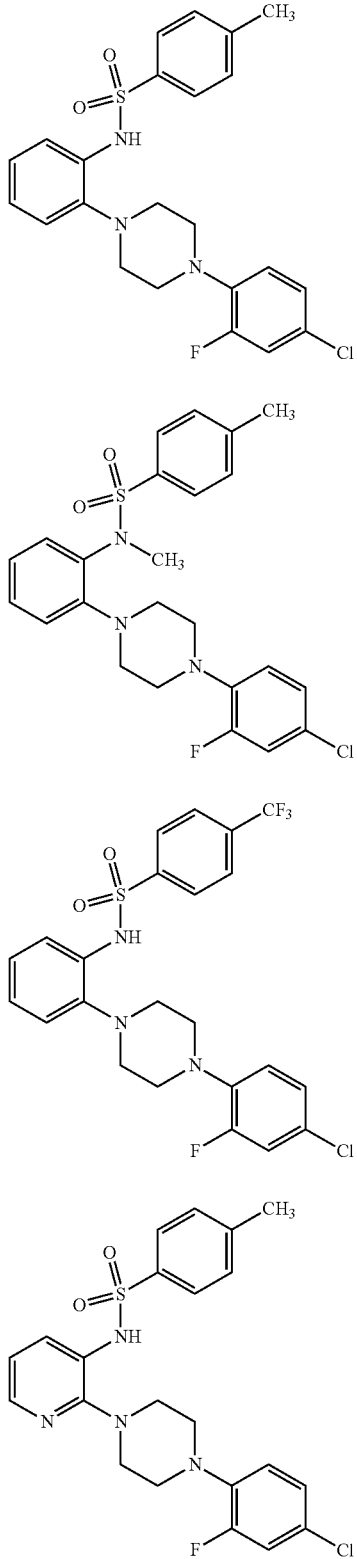
TABLE 1-continued
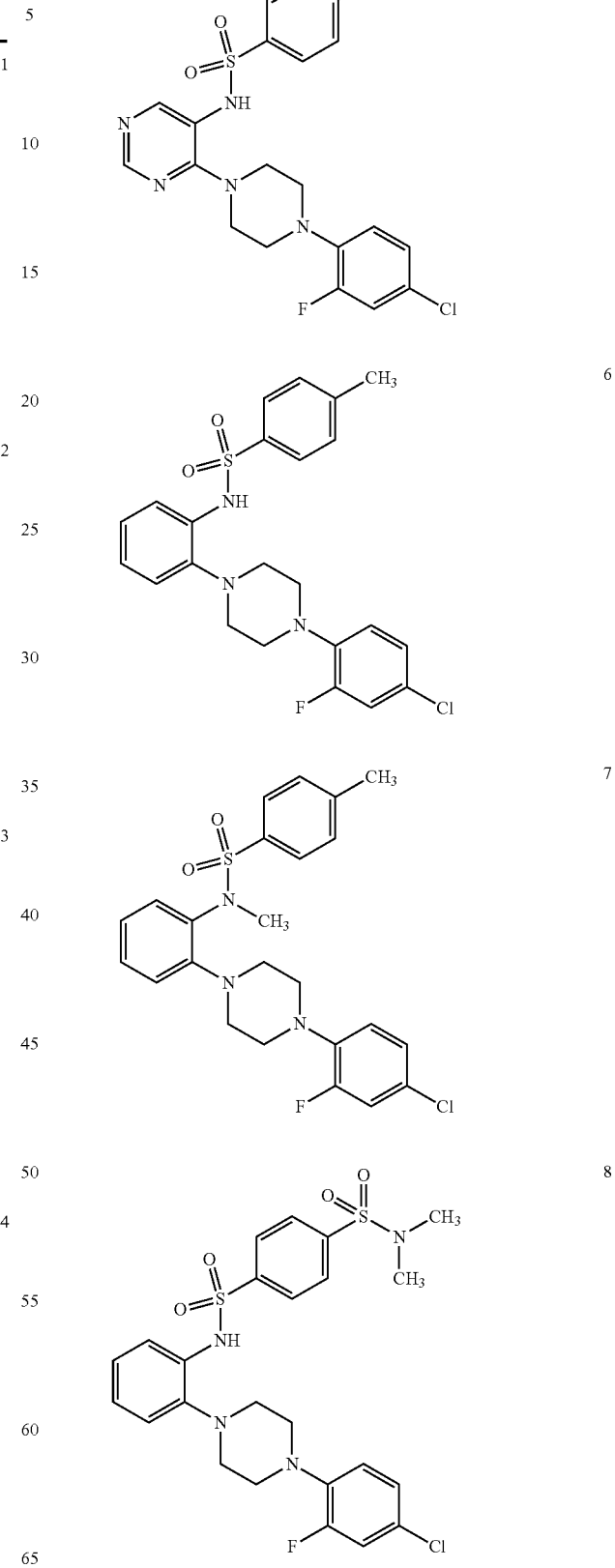

TABLE 1-continued
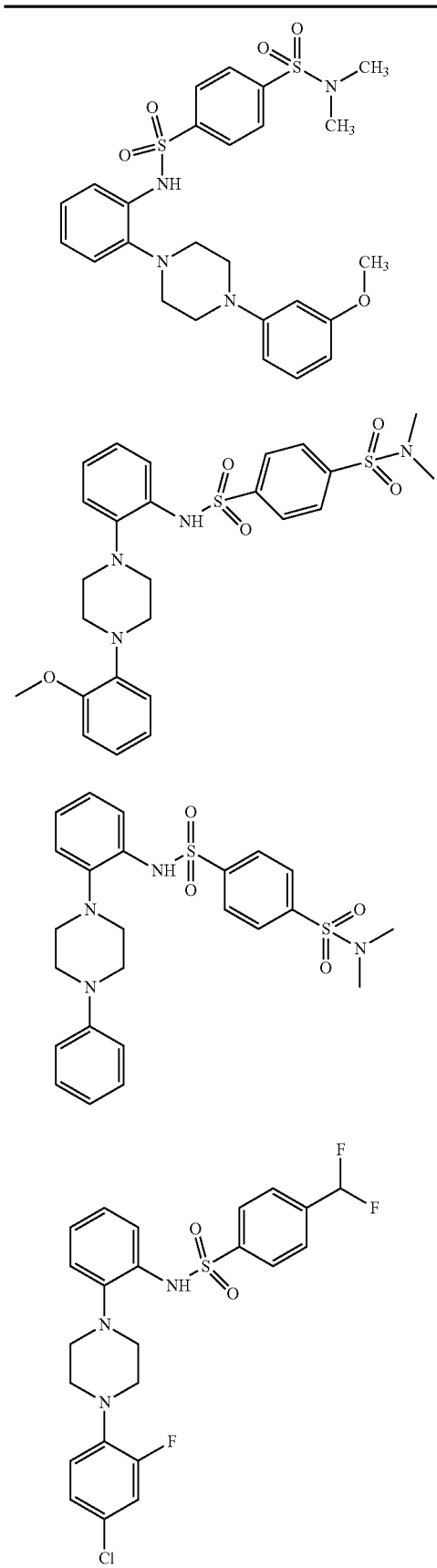
TABLE 1-continued
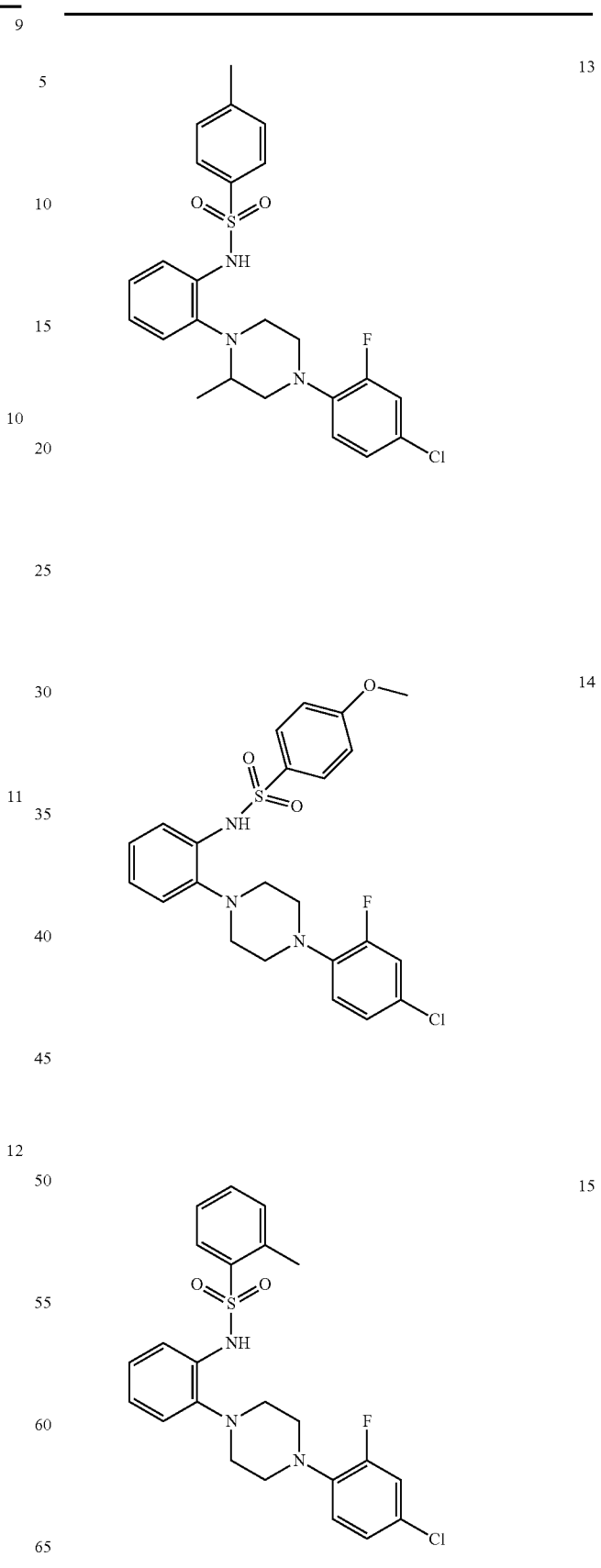

TABLE 1-continued

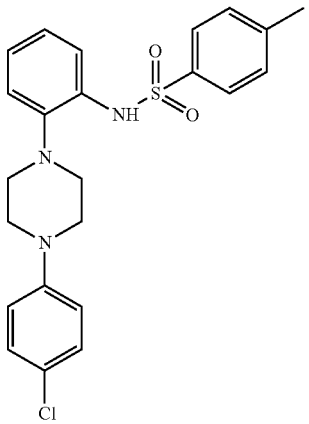 [SMILES: Cc1ccc(S(=O)(=O)Nc2ccccc2N2CCN(c3ccc(Cl)cc3)CC2)cc1]

16

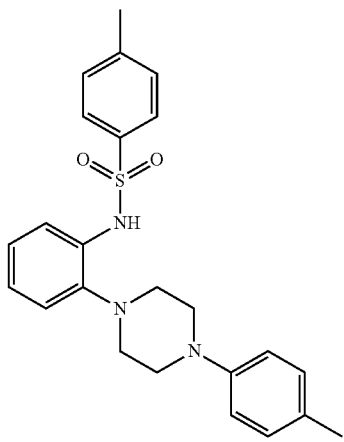 [SMILES: Cc1ccc(N2CCN(c3ccccc3NS(=O)(=O)c3ccc(C)cc3)CC2)cc1]

17

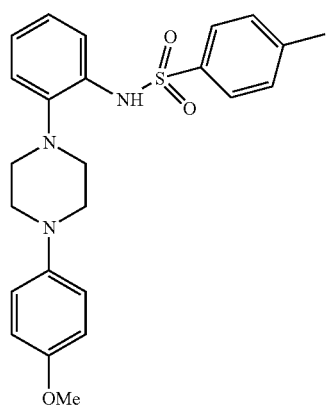 [SMILES: COc1ccc(N2CCN(c3ccccc3NS(=O)(=O)c3ccc(C)cc3)CC2)cc1]

18

TABLE 1-continued

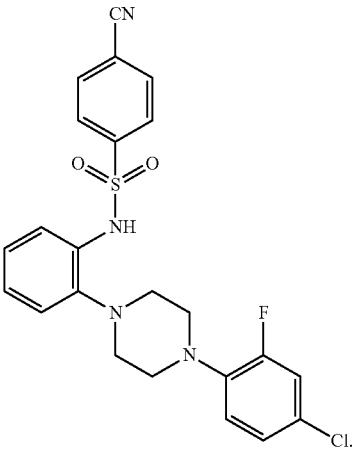 [SMILES: N#Cc1ccc(S(=O)(=O)Nc2ccccc2N2CCN(c3ccc(Cl)cc3F)CC2)cc1]

19

Representative compounds are listed below:
N-[2-[4-(4-Chloro-2-fluorophenyl)-1-piperazinyl]phenyl]-4-methylbenzenesulfonamide (1);
N-[2-[4-(4-Chloro-2-fluorophenyl)-1-piperazinyl]phenyl]-N,4-dimethylbenzenesulfonamide (2);
N-[2-[4-(4-Chloro-2-fluorophenyl)-1-piperazinyl]phenyl]-4-(trifluoromethyl)benzenesulfonamide (3);
N-[2-[4-(4-Chloro-2-fluorophenyl)-1-piperazinyl]-3-pyridyl]-4-methylbenzenesulfonamide (4);
N-[4-[4-(4-Chloro-2-fluorophenyl)-1-piperazinyl]-5-pyrimidyl]-4-methylbenzenesulfonamide (5);
1-(4-Chloro-2-fluorophenyl)-4-[2-(tosylmethyl)phenyl]piperazine (6);
1-(4-Chloro-2-fluorophenyl)-4-[2-(1-tosylethyl)phenyl]piperazine (7);
N1-[2-[4-(4-Chloro-2-fluorophenyl)-1-piperazinyl]phenyl]-N4,N4-dimethylbenzene-1,4-disulfonamide (8);
N1-[2-[4-(3-Methoxyphenyl)-1-piperazinyl]phenyl]-N4,N4-dimethylbenzene-1,4-disulfonamide (9);
N1-[2-[4-(2-Methoxyphenyl)-1-piperazinyl]phenyl]-N4,N4-dimethylbenzene-1,4-disulfonamide (10);
N1,N1-Dimethyl-N4-[2-(4-phenyl-1-piperazinyl)phenyl]benzene-1,4-disulfonamide (11);
N-[2-[4-(4-Chloro-2-fluorophenyl)-1-piperazinyl]phenyl]-4-(difluoromethyl)benzenesulfonamide (12);
N-[2-[4-(4-Chloro-2-fluorophenyl)-2-methyl-1-piperazinyl]phenyl]-4-methylbenzenesulfonamide (13);
N-[2-[4-(4-Chloro-2-fluorophenyl)-1-piperazinyl] phenyl]-4-methoxybenzenesulfonamide (14);
N-[2-[4-(4-Chloro-2-fluorophenyl)-1-piperazinyl]phenyl]-2-methylbenzenesulfonamide (15);
N-[2-[4-(4-Chlorophenyl)-1-piperazinyl]phenyl]-4-methylbenzenesulfonamide (16);
4-Methyl-N-[2-[4-(p-tolyl)-1-piperazinyl] phenyl] benzenesulfonamide (17);
N-[2-[4-(4-Methoxyphenyl)-1-piperazinyl]phenyl]-4-methylbenzenesulfonamide (18);
N-[2-[4-(4-Chloro-2-fluorophenyl)-1-piperazinyl] phenyl]-4-cyanobenzenesulfonamide (19).

The synthesis of compounds of the formulae herein can be readily effected by synthetic chemists of ordinary skill. Relevant procedures and intermediates are disclosed, for instance, herein. Each of the patents, patent applications, and publications, whether in traditional journals or available only through the internet, referred to herein, is incorporated in its entirety by reference.

Other approaches to synthesizing compounds of the formulae herein can readily be adapted from references cited herein. Variations of these procedures and their optimization are within the skill of the ordinary practitioner.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (e.g., $R^1$, $R^2$, R, R', X, etc.) or not. The suitability of a chemical group in a compound structure for use in synthesis of another compound structure is within the knowledge of one of ordinary skill in the art. Additional methods of synthesizing compounds of the formulae herein and their synthetic precursors, including those within routes not explicitly shown in schemes herein, are within the means of chemists of ordinary skill in the art. Methods for optimizing reaction conditions, if necessary minimizing competing byproducts, are known in the art. The methods described herein may also additionally include steps, either before or after the steps described specifically herein, to add or remove suitable protecting groups in order to ultimately allow synthesis of the compounds herein. In addition, various synthetic steps may be performed in an alternate sequence or order to give the desired compounds. Synthetic chemistry transformations and protecting group methodologies (protection and deprotection) useful in synthesizing the applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, $3^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The methods delineated herein contemplate converting compounds of one formula to compounds of another formula. The process of converting refers to one or more chemical transformations, which can be performed in situ, or with isolation of intermediate compounds. The transformations can include reacting the starting compounds or intermediates with additional reagents using techniques and protocols known in the art, including those in the references cited herein. Intermediates can be used with or without purification (e.g., filtration, distillation, sublimation, crystallization, trituration, solid phase extraction, and chromatography).

Combinations of substituents and variables envisioned by this invention are only those that result in the formation of stable compounds.

The invention also provides compositions comprising an effective amount of a compound of any of the formulae herein, or a pharmaceutically acceptable salt, solvate, hydrate, polymorph or prodrug, if applicable, of said compound; and an acceptable carrier. Preferably, a composition of this invention is formulated for pharmaceutical use ("a pharmaceutical composition"), wherein the carrier is a pharmaceutically acceptable carrier. The carrier(s) must be "acceptable" in the sense of being compatible with the other ingredients of the formulation and, in the case of a pharmaceutically acceptable carrier, not deleterious to the recipient thereof in amounts typically used in medicaments.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch). Other formulations may conveniently be presented in unit dosage form, e.g., tablets and sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers or both, and then if necessary shaping the product.

In certain preferred embodiments, the compound is administered orally. Compositions of the present invention suitable for oral administration may be presented as discrete units such as capsules, sachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc. Soft gelatin capsules can be useful for containing such suspensions, which may beneficially increase the rate of compound absorption.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets optionally may be coated or scored and may be formulated so as to provide slow or controlled release of the active ingredient therein. Methods of formulating such slow or controlled release compositions of pharmaceutically active ingredients, such as those herein and other compounds known in the art, are known in the art and described in several issued US Patents, some of which include, but are not limited to, U.S. Pat. Nos. 4,369,172; and 4,842,866, and references cited therein. Coatings can be used for delivery of compounds to the intestine (see, e.g., U.S. Pat. Nos. 6,638,534, 5,217,720, and 6,569,457, 6,461,631, 6,528,080, 6,800,663, and references cited therein). A useful formulation for the compounds of this invention is the form of enteric pellets of which the enteric layer comprises hydroxypropylmethylcellulose acetate succinate.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for topical administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyl-dodecanol, benzyl alcohol and water. The pharmaceutical compositions of this invention may also be topically applied to the lower intestinal tract by rectal suppository formulation or in a suitable enema formulation. Topically-transdermal patches and iontophoretic administration are also included in this invention.

Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or central nervous system) relative to the parent species. Preferred prodrugs include derivatives where a group that enhances aqueous solubility or active transport through the gut membrane is appended to the structure of formulae described herein. See, e.g., Alexander, J. et al. *Journal of Medicinal Chemistry* 1988, 31, 318-322; Bundgaard, H. *Design of Prodrugs*; Elsevier: Amsterdam, 1985; pp 1-92; Bundgaard, H.; Nielsen, N. M. *Journal of Medicinal Chemistry* 1987, 30, 451-454; Bundgaard, H. *A Textbook of Drug Design and Development*; Harwood Academic Publ.: Switzerland, 1991; pp 113-191; Digenis, G. A. et al. *Handbook of Experimental Pharmacology* 1975, 28, 86-112; Friis, G. J.; Bundgaard, H. *A Textbook of Drug Design and Development*; 2 ed.; Overseas Publ.: Amsterdam, 1996; pp 351-385; Pitman, I. H. *Medicinal Research Reviews* 1981, 1, 189-214.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

In another embodiment, a composition of the present invention further comprises a second therapeutic agent. The second therapeutic agent includes any compound or therapeutic agent known to have or that demonstrates advantageous properties when administered alone or with a compound of any of the formulae herein. Drugs that could be usefully combined with these compounds include other kinase inhibitors and/or other chemotherapeutic agents for the treatment of the diseases and disorders discussed above.

Such agents are described in detail in the art. Preferably, the second therapeutic agent is an agent useful in the treatment or prevention of a disease or condition selected from cancer.

Even more preferably the second therapeutic agent co-formulated with a compound of this invention is an agent useful in the treatment of TRPML mediated disease/disorders.

In another embodiment, the invention provides separate dosage forms of a compound of this invention and a second therapeutic agent that are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., (1966) Cancer Chemother Rep 50: 219. Body surface area may be approximately determined from height and weight of the patient. See, e.g., Scientific Tables, Geigy Pharmaceuticals, Ardley, N.Y., 1970, 537. An effective amount of a compound of this invention can range from about 0.001 mg/kg to about 500 mg/kg, more preferably 0.01 mg/kg to about 50 mg/kg, more preferably 0.1 mg/kg to about 2.5 mg/kg. Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Lorna Linda, Calif. (2000), each of which references are entirely incorporated herein by reference.

It is expected that some of the second therapeutic agents referenced above will act synergistically with the compounds of this invention. When this occurs, its will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

According to another embodiment, the invention provides a method of treating a subject suffering from or susceptible to a disease or disorder or symptom thereof (e.g., those delineated herein) comprising the step of administering to said subject an effective amount of a compound or a composition of this invention. Some diseases are well known in the art and are also disclosed herein.

In one aspect, the method of treating involves treatment of a disorder that is mediated by the TRPMLs.

In another aspect, the invention provides a method of treating a disease in a subject comprising administering to the subject a compound of formula I.

In another aspect, invention provides a method of treating a disease in a subject comprising administering to the subject a composition comprising a compound of formula I.

In certain embodiments, the disease is one of the lysosomal storage diseases, such as Niemen-Pick C (NPC) disease.

In another embodiment, the disease is age-related common neurodegenerative disease, such as AD, PD, and HD.

In yet another embodiment, the disease is type IV Mucolipidosis (ML4), a neurodegenerative LSD caused by human mutations in TRPML1.

In a further embodiment, the disease is related to reactive oxygen species (ROS) or oxidative stress.

In another aspect, the invention provides a method of using a compound of formula I as an anti-ageing agent.

In another further embodiment, the method involves using a TRPML1 agonist as an anti-ageing agent.

In another embodiment, the invention provides a method of modulating the activities of TRPMLs in a cell comprising contacting a cell with one or more compounds of any of the formulae herein.

In another embodiment, the above method of treatment comprises the further step of co-administering to said patient one or more second therapeutic agents. The choice of second therapeutic agent may be made from any second therapeutic agent known to be useful for indications herein. Additional therapeutic agents include but are not limited to agents for treatment of diseases, disorders or symptoms thereof, including, e.g. cyclodextrin for NPC-type lysosome storage disease.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention comprising both a compound of the invention and a second therapeutic agent to a subject does not preclude the separate administration of that same therapeutic agent, any other second therapeutic agent or any compound of this invention to said subject at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of any of the formulae herein alone or together with one or more of the above-described second therapeutic agents in the manufacture of a medicament, either as a single composition or as separate dosage forms, for treatment or prevention in a subject of a disease, disorder or symptom set forth above. Another aspect of the invention is a compound of the formulae herein for use in the treatment or prevention in a subject of a disease, disorder or symptom thereof delineated herein.

In other aspects, the methods herein include those further comprising monitoring subject response to the treatment administrations. Such monitoring may include periodic sampling of subject tissue, fluids, specimens, cells, proteins, chemical markers, genetic materials, etc. as markers or indicators of the treatment regimen. In other methods, the subject is prescreened or identified as in need of such treatment by assessment for a relevant marker or indicator of suitability for such treatment.

In one embodiment, the invention provides a method of monitoring treatment progress. The method includes the step of determining a level of diagnostic marker (Marker) (e.g., any target or cell type delineated herein modulated by a compound herein) or diagnostic measurement (e.g., screen, assay) in a subject suffering from or susceptible to a disorder or symptoms thereof delineated herein, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

In certain method embodiments, a level of Marker or Marker activity in a subject is determined at least once. Comparison of Marker levels, e.g., to another measurement of Marker level obtained previously or subsequently from the same patient, another patient, or a normal subject, may be useful in determining whether therapy according to the invention is having the desired effect, and thereby permitting adjustment of dosage levels as appropriate. Determination of Marker levels may be performed using any suitable sampling/expression assay method known in the art or described herein. Preferably, a tissue or fluid sample is first removed from a subject. Examples of suitable samples include blood, urine, tissue, mouth or cheek cells, and hair samples containing roots. Other suitable samples would be known to the person skilled in the art. Determination of protein levels and/or mRNA levels (e.g., Marker levels) in the sample can be performed using any suitable technique known in the art, including, but not limited to, enzyme immunoassay, ELISA, radiolabelling/assay techniques, blotting/chemiluminescence methods, real-time PCR, and the like.

The present invention also provides kits for use to treat diseases, disorders, or symptoms thereof, including those delineated herein. These kits comprise: a) a pharmaceutical composition comprising a compound of any of the formula herein or a salt thereof; or a prodrug, or a salt of a prodrug thereof; or a hydrate, solvate, or polymorph thereof, wherein said pharmaceutical composition is in a container; and b) instructions describing a method of using the pharmaceutical composition to treat the disease, disorder, or symptoms thereof, including those delineated herein.

The container may be any vessel or other sealed or sealable apparatus that can hold said pharmaceutical composition. Examples include bottles, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. Preferably, the container is a blister pack.

The kit may additionally comprising information and/or instructions for the physician, pharmacist or subject. Such memory aids include numbers printed on each chamber or division containing a dosage that corresponds with the days of the regimen which the tablets or capsules so specified should be ingested, or days of the week printed on each chamber or division, or a card which contains the same type of information.

All references cited herein, whether in print, electronic, computer readable storage media or other form, are expressly incorporated by reference in their entirety, including but not limited to, abstracts, articles, journals, publications, texts, treatises, technical data sheets, internet web sites, databases, patents, patent applications, and patent publications.

EXAMPLES

Example 1: Synthesis of N-[2-[4-(4-Chloro-2-fluorophenyl)-1-piperazinyl]phenyl]-4-methylbenzenesulfonamide (1)

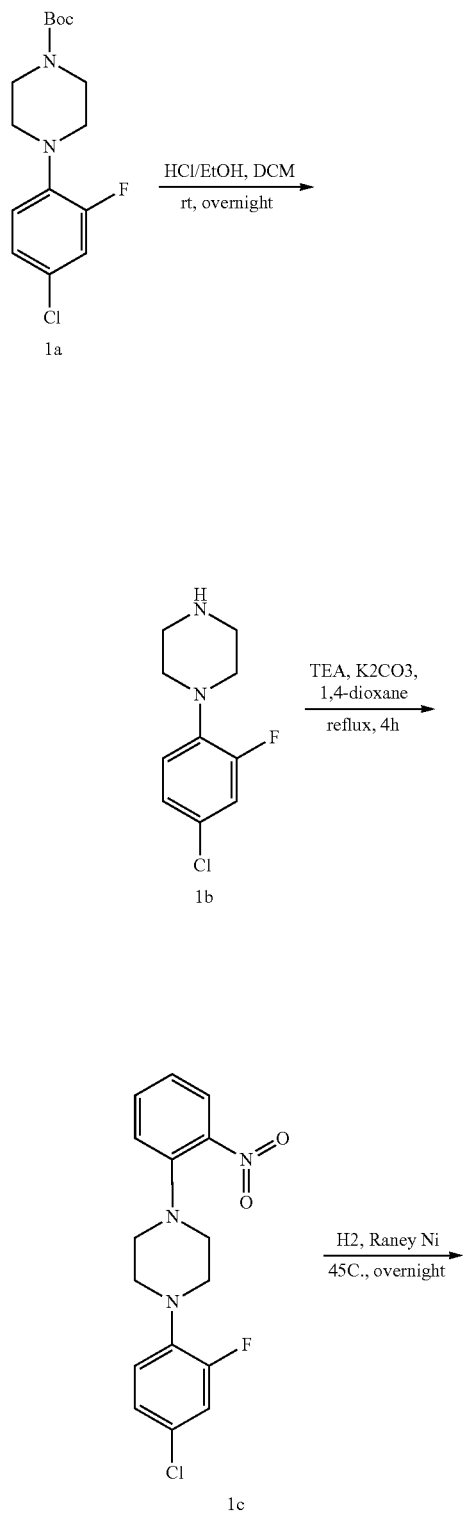

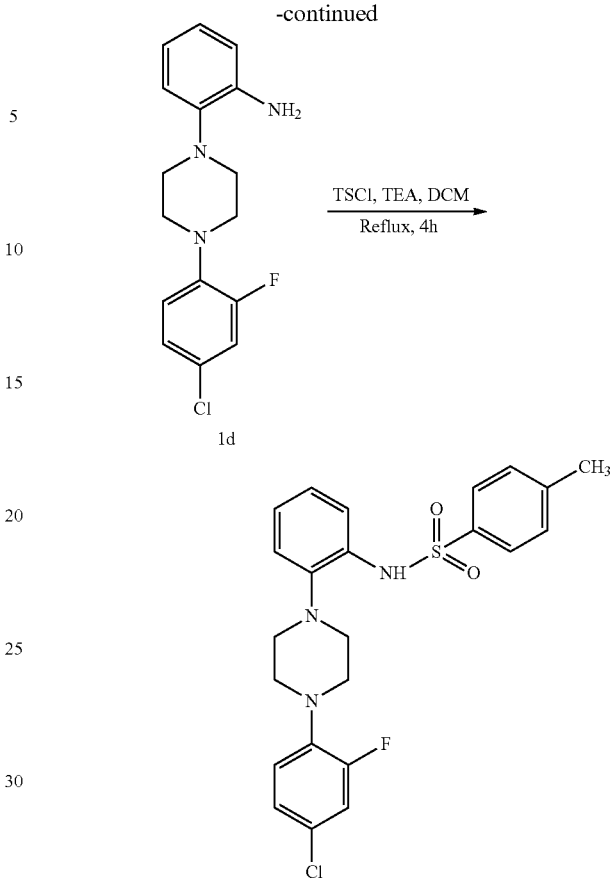

Step 1. The compound 1a (5 g, 1 eq) was dissolved in dichloromethane (300 ml). 30% HCl/EtOH (15 g, 5 eq) was added. After stirring overnight at room temperature, compound 1b as white solid was collected by filtration. It was used directly in the next step without further purification.

Step 2. The mixture of compound 1b (1 eq) and triethylamine (7.5 g, 3 eq) was dissolved in 1,4-dioxane (100 m). After stirring 15 min, $K_2CO_3$ (8.4 g, 1 eq) and 1-fluoro-2-nitro-benzene (3.1 g, 0.9 eq) were added. The mixture was reflux under nitrogen atmosphere for 4 h. Then it was cooled to 10° C., poured to 200 ml water and extracted with ethyl acetate. The organic layer was washed with brine, dried over $Na_2SO_4$ and concentrated to give compound 1e (5.3 g, yield of 2 steps 64%). MS-ESI: [M+1]+=336.7.

Step 3. The mixture of compound 1c (5.3 g) was dissolved in methanol (100 ml). Raney Ni (2 g) was added. Hydrogenation was carried out under the pressure of 30 bars for 15 h at 45° C. The catalyst was filtered and washed three times with methanol (3×20 mL). The filtrates were combined and concentrated under vacuum. The resulting crude product was purified by silica column chromatography to give compound 1d (2.9 g, Yield 60%). MS-ESI: [M+1]+=306.7.

Step 4: The mixture of compound 1d (1 g, 1 eq) and triethylamine (1 g, 3 eq) was dissolved in dichloromethane (50 ml). TsCl (1 eq) was added. After reflux overnight, the solution was concentrated under vacuum. The resulting crude product was purified by silica column chromatography to give compound 1 as white solid (0.16 g). MS-ESI: [M+1]+=460.5. 1H NMR (300 MHz, CDCl3): δ 8.05 (s, 1H), 7.73 (d, 2H), 7.63 (d, 1H), 7.28-7.05 (m, 7H), 6.96 (t, 1H), 3.16 (s, 4H), 2.76 (s, 4H), 2.39 (s, 3H).

Example 2: Synthesis of N-[2-[4-(4-Chloro-2-fluorophenyl)-1-piperazinyl]phenyl]-N,4-dimethylbenzenesulfonamide (2)

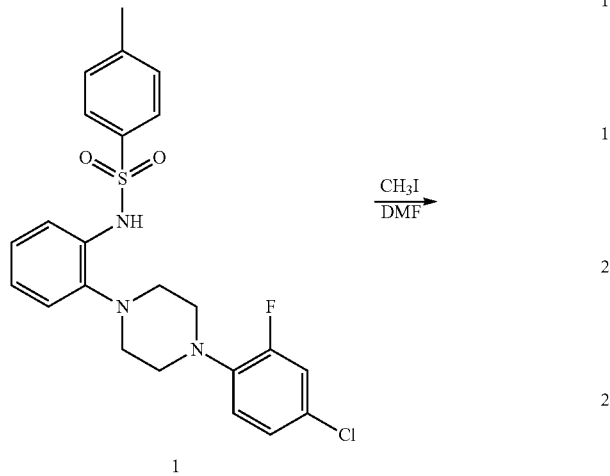

Example 3: Synthesis of N-[2-[4-(4-Chloro-2-fluorophenyl)-1-piperazinyl]phenyl]-4-(trifluoromethyl)benzenesulfonamide (3)

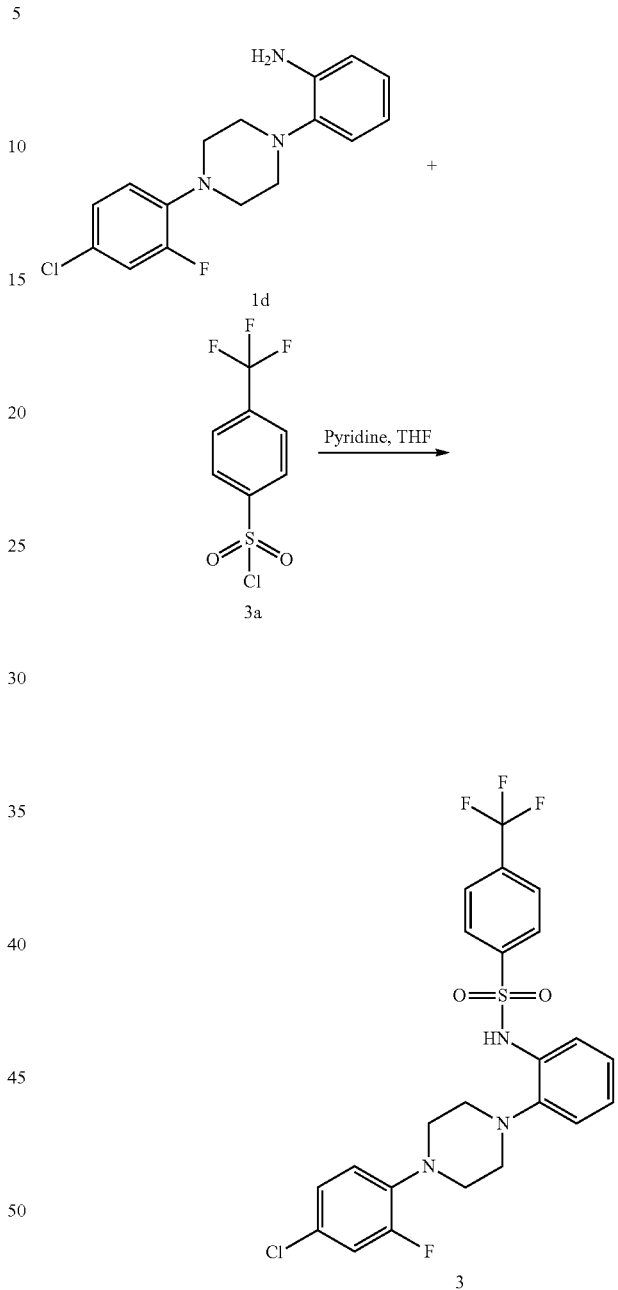

Step 1: To a 50 mL round-bottom flask was added DMF 20 mL, N-[2-[4-(4-Chloro-2-fluorophenyl)-1-piperazinyl]phenyl]-4-methylbenzenesulfonamide (1) (0.4 g, 0.87 mmol, 1.0 eq) and potassium carbonate (0.361 g, 2.61 mmol, 3 eq) was dropped into the stirred mixture at room temperature for 1 h. CH$_3$I (0.37 mg, 2.61 mmol, 3 eq) was dropped into the stirred mixture at room temperature for 2 h. The solution was concentrated and subjected to silica gel eluted to afford the title compound 2 (160 mg, HPLC: 95%) as a white solid. Yield: 37.8%. MS-ESI: [M+1]$^+$=474.7. $^1$H NMR (400 MHz, DMSO) δ 7.71 (d, 2H), 7.47 (d, 2H), 7.37 (dd, 2.4 Hz, 1H), 7.29 (dd, 1H), 7.23 (m, 2H), 7.10 (t, 1H), 6.99 (t, 1H), 6.87 (dd, 1H), 3.16 (s, 3H), 3.11 (d, 8H), 2.43 (s, 3H).

Step 1: To a 100 mL round-bottom flask was added 30 mL THF, 2-[4-(4-chloro-2-fluorophenyl)piperazinyl]phenylamine (1d) (0.5 g, 1.0 eq), pyridine (0.65 g, 5 eq) and compound 3a (0.48 g, 1.2 eq). The reaction was heated to reflux for 15 h. TLC showed the reaction was uncompleted. Another compound 3a (0.2 g, 0.5 eq) was added. The reaction was heated to reflux for 24 h. The reaction mixture was concentrated in vacuum and purified by column chromatography on silica gel eluted to afford the title compound 3 (0.7 g). Yield: 83%. MS-ESI: [M-1]$^-$=512.4. $^1$H NMR (300 MHz, CDCl3): δ 8.11 (s, 1H), 7.98 (d, 2H), 7.74 (d, 2H), 7.60 (dd, 1H), 7.24-7.08 (m, 5H), 6.94 (t, 1H), 3.15 (t, 4H), 2.76 (t, 4H).

Example 4: Synthesis of N-[2-[4-(4-Chloro-2-fluorophenyl)-1-piperazinyl]-3-pyridyl]-4-methylbenzenesulfonamide (4)

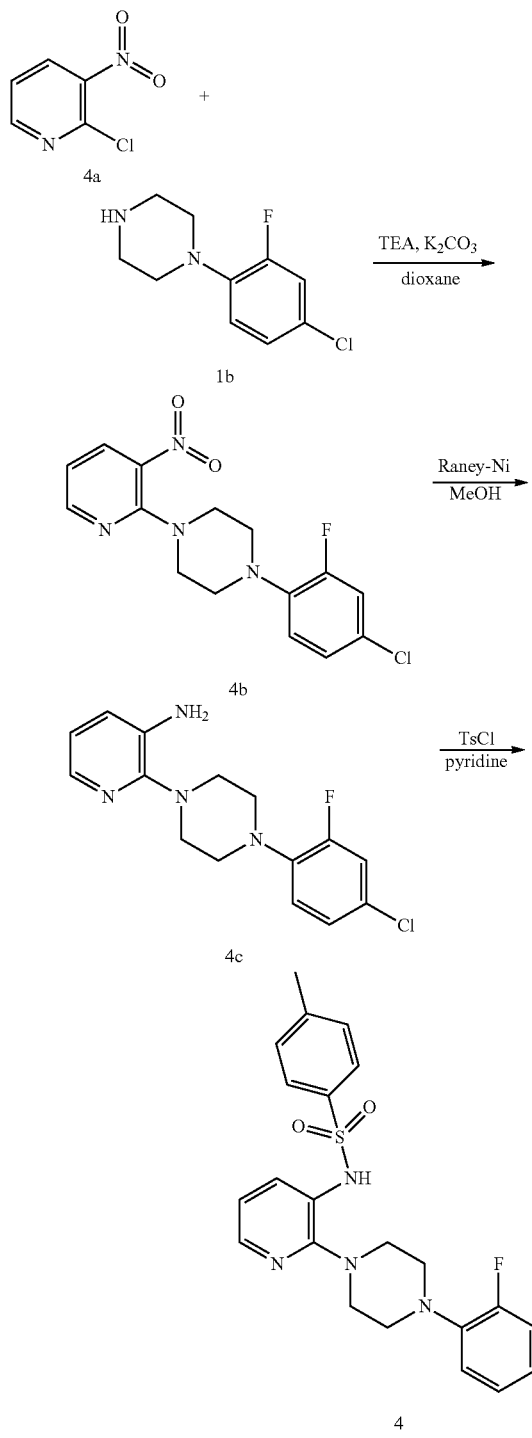

Step 1: To a 250 mL round-bottom flask was added 1,4-dioxane 20 mL, compound 1b (4.5 g, 0.021 mol, 1.0 eq) and TEA (6.37 g, 0.063 mol, 3 eq) was dropped into the stirred mixture at room temperature for 15 min. And potassium carbonate (7.27 g, 0.0526 mol, 2.5 eq) and compound 4a (3 g, 0.0189 mol, 0.9 eq) were dropped into the stirred mixture and refluxed for 3 h. This reaction was added water 200 mL and extracted with EA (10 mL*3), the organic solution was dried over sodium sulfate, filtered, and concentrated to afford the title compound 4b (5 g, HPLC: 98%) Yield: 71%.

Step 2: To a 50 mL round-bottom flask was added methanol 20 mL, compound 4b (5 g, 0.014 mol, 1.0 eq), Raney-Nickel catalyst (2 g) was dropped into the stirred mixture at room temperature for overnight. The solution was filtered, and concentrated to afford the title compound 4c (3 g, HPLC: 94%) Yield: 70%

Step 3: To a 50 mL round-bottom flask was added pyridine 20 mL, compound 4c (1 g, 3.27 mmol, 1.0 eq) and TsCl (0.8 g, 4.2 mmol, 1.3 eq) was dropped into the stirred mixture at room temperature for 2 h. The solution was concentrated and subjected to silica gel eluted to afford the title compound 4 (567 mg, HPLC: 96%) as a white solid. Yield: 38%. MS-ESI: [M+1]$^+$=461.7. $^1$H NMR (400 MHz, DMSO): δ 9.43 (s, 1H), 8.07 (dd, 1H), 7.68 (d, 2H), 7.43-7.29 (m, 2H), 7.22 (dd, 1H), 7.07 (t, 1H), 6.93 (dd, 1H), 6.52 (d, 1H), 4.04 (q, 1H), 3.24-3.11 (m, 4H), 3.07-2.96 (m, 4H), 2.36 (s, 3H)

Example 5: Synthesis of N-[4-[4-(4-Chloro-2-fluorophenyl)-1-piperazinyl]-5-pyrimidyl]-4-methylbenzenesulfonamide (5)

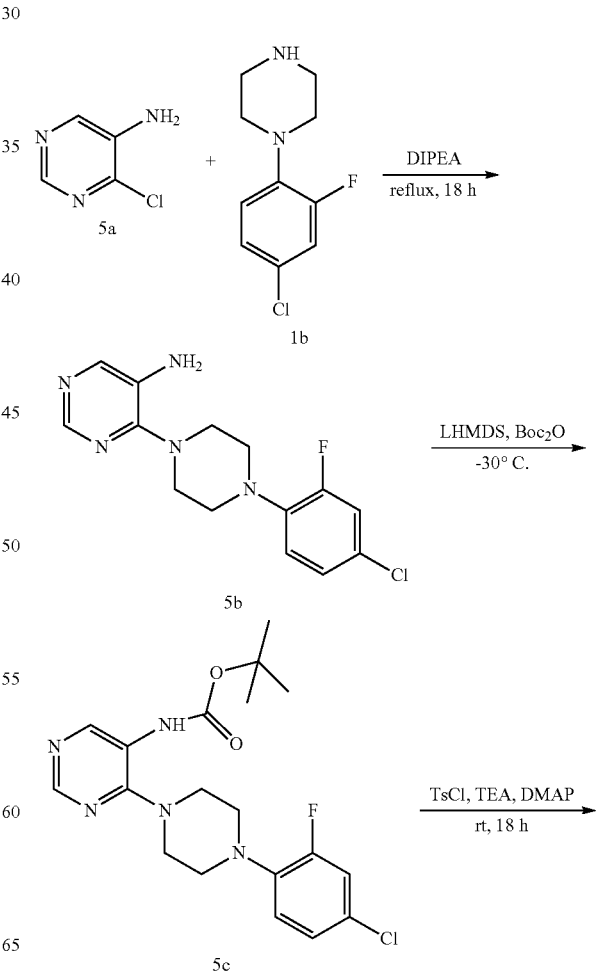

-continued

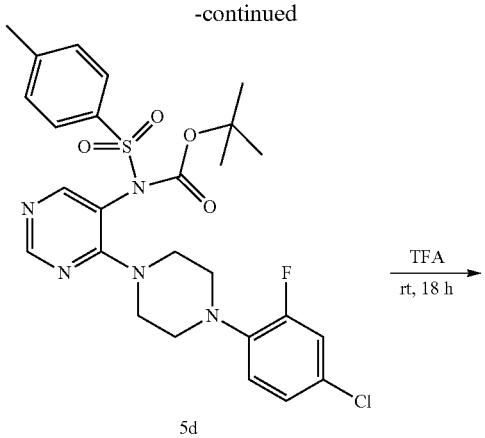

5d

↓ TFA
rt, 18 h

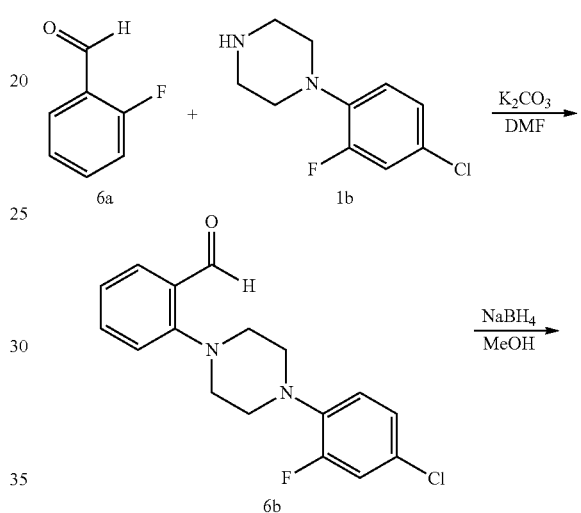

5

Step 1: To a 50 mL round-bottom flask was added 20 mL 1, 4-Dioxane, compound 5a (885 mg, 6.83 mmol, 1.0 eq), compound 1b (1.61 g, 7.52 mmol, 1.1 eq) and DIPEA (1.32 g, 10.25 mmol, 1.5 eq). The reaction was heated to reflux for 18 h. TLC (PE:EA=1:1) showed the reaction was completed. The reaction mixture was concentrated in vacuum and purified by column chromatography on silica gel eluted with PE:EA=3:1-1:1 to afford the title compound 5b (1.5 g, HPLC: 93%, Yield: 71.4%) as an orange solid.

Step 2: To a 100 mL three-necked flask was added 20 mL THF and compound 5b (0.8 g, 2.60 mol, 1.0 eq). The mixture was cooled to −30° C. with nitrogen. Then 1M LHMDS (7.8 mL, 7.80 mmol, 3.0 eq) was dropped to the mixture. The mixture was stirred at −30° C. for 30 min. Then Boc$_2$O (681 mg, 3.12 mmol, 1.2 eq) in 4 mL THF was dropped to the mixture. The reaction was stirred at RT for 2 h. The solution was added 20 mL water and extracted with EA (5 mL*5). The organic layer was dried, concentrated in vacuum and purified by column chromatography on silica gel eluted with PE:EA=5:1-3:1 to afford the compound 5c (280 mg, HPLC: 85%, Yield: 26.4%) as an oil.

Step 3: To a 25 mL round-bottom flask was added 2 mL DCM, compound 5c (110 mg, 0.270 mmol, 1.0 eq), TEA (82 mg, 0.810 mmol, 3.0 eq), TsCl (57 mg, 0.297 mmol, 1.10 eq) and DMAP (3 mg, 0.027 mmol, 0.1 eq). The reaction was stirred at RT for 18 h. Then 2 mL DCM and TsCl (57 mg, 0.297 mmol, 1.10 eq) were added. The reaction was heated to 50° C. for 18 h. The reaction mixture was concentrated in vacuum and purified by column chromatography on silica gel eluted with PE:EA=1:1 to afford the title compound 5d (100 mg, crude). Yield: 66.2%.

Step 4: To a 25 mL round-bottom flask was added 2 mL DCM and compound 5d (100 mg, 0.071 mmol, 1.0 eq). Then TFA (2.0 mL) was dropped to the mixture. The reaction was stirred at RT for 18 h. The reaction mixture was concentrated in vacuum and purified by column chromatography on silica gel eluted with PE:EA=1:1 to afford the title compound 5 (68 mg, HPLC: 87%, Yield: 82.9%). MS-ESI: [M+1]$^+$=462.7. $^1$H NMR (300 MHz, CDCl$_3$): δ 8.41 (s, 1H), 7.68-7.36 (m, 6H), 7.22-7.05 (m, 2H), 6.98-6.84 (m, 1H), 4.43 (br, 4H), 3.24 (br, 4H), 2.43 (s, 3H).

Example 6: Synthesis of 1-(4-Chloro-2-fluorophenyl)-4-[2-(tosylmethyl) phenyl]piperazine (6)

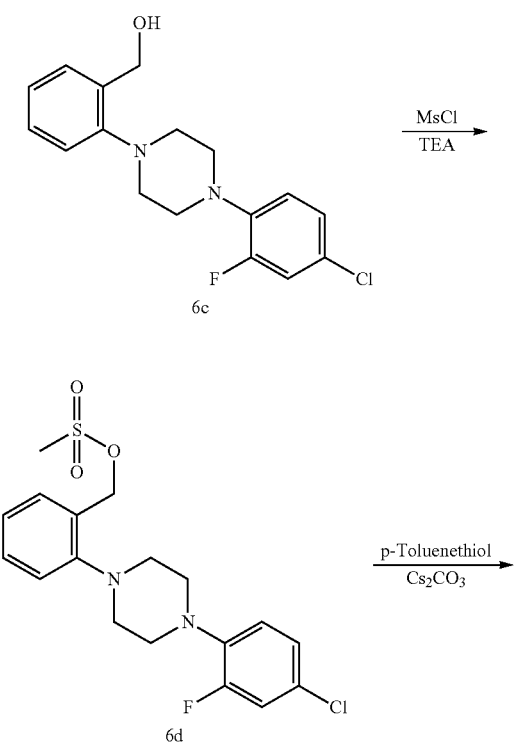

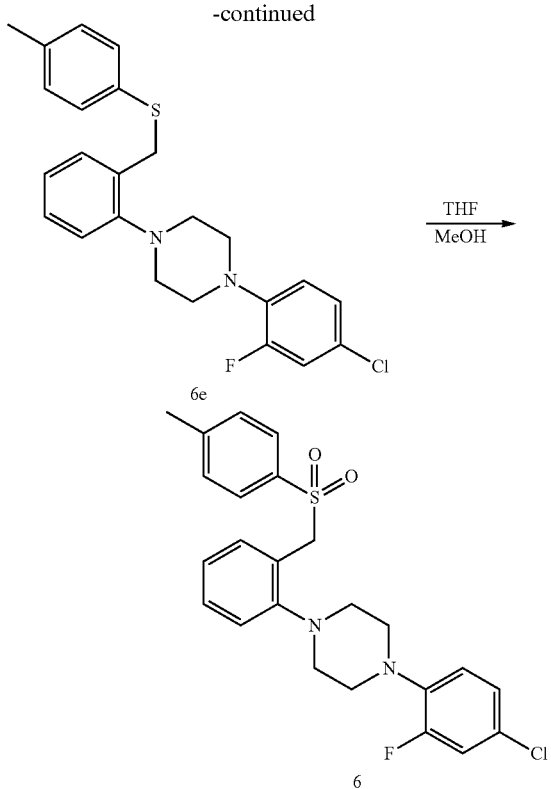

Step 1: To a 100 mL round-bottom flask was added 30 mL DMF, compound 6a (4.0 g, 32.2 mmol, 1.0 eq), compound 1b (5.5 g, 25.7 mmol, 0.8 eq), K$_2$CO$_3$ (13.4 g, 96.6 mmol, 3.0 q), the temperature was kept at 140° C. for overnight, TLC (PE:EA=10:1, R$_f$=0.4) showed the reaction was having a new point. The reaction was allowed to cool to room temperature and the reaction mixture was poured onto 150 mL ice water, the mixture was stirred for 10 min, extracted with EA (50 mL*3). the combined organic layers were washed with brine aqueous solution and dried over Na$_2$SO$_4$, filtered and concentrated in vacuum. The residue was purified by column chromatography on silica gel to yield the title product 6b (4.2 g, TLC: 95%) as a light-brown solid. Yield: 41.2%.

Step 2: To a 100 mL round-bottom flask was added compound 6b (4.2 g, 13.2 mmol, 1.0 eq) and 40 mL MeOH. Sodium borohydride (1000 mg, 26.4 mmol, 2.0 eq) was added into the stirred mixture portionwise under ice batch (T<10° C.). After stirring at room temperature for 1 h, TLC (PE:EA=10:1, R$_f$=0.05) showed the reaction was completed the reaction mixture was poured onto 80 mL water, the mixture was stirred for 10 min, extracted with EA (80 mL*2). the combined organic layers were washed with brine aqueous solution and dried over Na$_2$SO$_4$, filtered and concentrated in vacuum to obtain the product 6c (4.1 g) which was used in the next step without purification. Yield: 97.6%.

Step 3: To a 50 mL round-bottom flask was added 10 mL DCM. Compound 6c (640 mg, 2.0 mmol, 1.0 eq), TEA (242.8 g, 2.4 mmol, 1.2 eq), MsCl (252 mg, 2.2 mmol, 1.1 q) were added dropwise into the stirred mixture under ice batch. Then the reaction kept the temperature for 3 h, TLC (PE:EA=20:1) showed the reaction was having a new point. The mixture was concentrated in vacuum under low temperature (T<10° C.). The crude product (6d) was used to the next step without purification.

Step 4: To a 50 mL round-bottom flask was added 10 mL DMF, compound 6d (2.0 mmol, 1.0 eq), p-toluenethiol (298.1 mg, 2.4 mmol, 1.2 q) and Cs$_2$CO$_3$ (977.5 mg, 3.0 mmol, 1.5 q), the reaction was stirred at 90° C. for 2 h, TLC (PE:EA=30:1, R$_f$=0.6) showed the reaction was complete. The reaction was allowed to cool to room temperature and the reaction mixture was poured onto 100 mL water, the mixture was stirred for 10 min, extracted with EA (50 mL*2). The combined organic layers were washed with brine (50 mL*2) and dried over Na$_2$SO$_4$, filtered and concentrated in vacuum. The residue was purified by column chromatography on silica gel to yield the title product (600 mg, HPLC: 93%) as an off-white solid 6e. Yield: 70.4% (two steps).

Step 5: To a 50 mL round-bottom flask was added 20 mL methanol and 5 mL THF, To the stirred mixture was added compound 6e (600 mg, 1.41 mmol, 1.0 eq), the solution of SY004475 (1213.5 mg, 1.97 mmol, 1.4 eq) in 10 mL water was added dropwise into the mixture. The reaction was stirred at room temperature for overnight. TLC (PE:EA=5:1, R$_f$=0.35) showed the reaction was complete. 30 mL water was added to the reaction mixture and extracted with EA (50 mL*2). the combined organic layers were washed with brine (50 mL*1) and dried over Na$_2$SO$_4$, filtered and concentrated in vacuum. The residue was purified by column chromatography on silica gel to yield the title product 6 (80 mg, HPLC: 97%) as a pink solid. Yield: 12.3%. MS-ESI: [M+H]$^+$=459.7. $^1$H NMR (400 MHz, CDCl3): δ 7.52 (dd, 3H), 7.37 (t, 1H), 7.26-7.15 (m, 4H), 7.13-7.06 (m, 3H), 4.65 (s, 2H), 3.12 (s, 4H), 2.79 (s, 4H), 2.41 (s, 3H).

Example 7: Synthesis of 1-(4-Chloro-2-fluorophenyl)-4-[2-(1-tosylethyl) phenyl]piperazine (7)

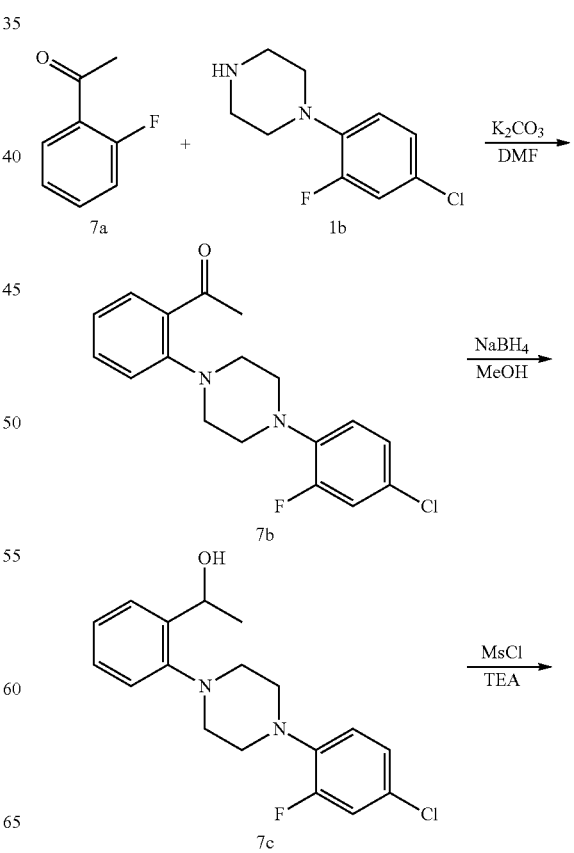

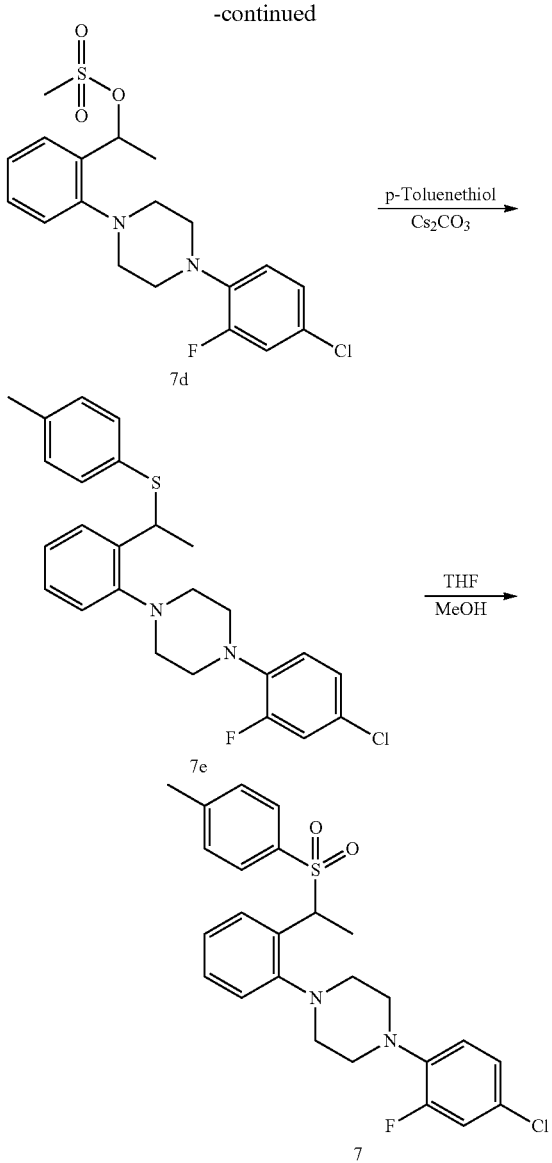

combined organic layers were washed with brine and dried over Na$_2$SO$_4$, filtered and concentrated in vacuum to obtained the crude product 7c (3.1 g) which was used in the next step without purification. Yield: 75.6%.

Step 3: To a 50 mL round-bottom flask was added 10 mL DCM, compound 7c (1.0 g, 2.99 mmol, 1.0 eq), TEA (363.4 mg, 3.59 mmol, 1.2 eq), MsCl (342.5 mg, 2.99 mmol, 1.0 q) was added dropwise into the stirred mixture under ice batch. Then the reaction kept the temperature for 3 h, TLC (PE:EA=20:1) showed the reaction was having a new point. The mixture was concentrated in vacuum under low temperature (T<10° C.). The crude product (7d) was used to the next step without purification.

Step 4: To a 50 mL round-bottom flask was added 10 mL DMF, compound 7d (2.99 mmol, 1.0 eq), p-toluenethiol (445.6 mg, 3.59 mmol, 1.2 q) and Cs$_2$CO$_3$ (1.46 g, 4.49 mmol, 1.5 q), the reaction was stirred at 90° C. for 2 h, TLC (PE:EA=30:1, R$_f$=0.65) showed the reaction was complete. The reaction was allowed to cool to room temperature and the reaction mixture was poured onto 100 mL water, the mixture was stirred for 10 min, extracted with EA (50 mL*2). the combined organic layers were washed with brine (50 mL*2) and dried over Na$_2$SO$_4$, filtered and concentrated in vacuum. The residue was purified by column chromatography on silica gel to yield the title product (410 mg, HPLC: 95%) as a white solid compound 7e. Yield: 31.0% (two steps).

Step 5: To a 50 mL round-bottom flask was added 8 mL methanol and 12 mL THF, To the stirred mixture was added compound 7e (410 mg, 0.93 mmol, 1.0 eq), the solution of potassium peroxomonosulfate (801.8 mg, 1.31 mmol, 1.4 eq) in 6 mL water was added dropwise into the mixture. The reaction was stirred at room temperature for overnight. TLC (PE:EA=5:1, R$_f$=0.4) showed the reaction was complete. 30 mL water was added to the reaction mixture and extracted with EA (50 mL*2). the combined organic layers were washed with brine (50 mL*1) and dried over Na$_2$SO$_4$, filtered and concentrated in vacuum. The residue was purified by column chromatography on silica gel to yield the title product 7 (135 mg, HPLC: 98%) as a white solid. Yield: 30.7%. MS-ESI: [M+H]$^+$=473.7. $^1$H NMR (400 MHz, CDCl3): δ 7.68 (dd, 1H), 7.46 (d, 2H), 7.35 (td, 1H), 7.26 (d, 2H), 7.20-7.09 (m, 5H), 5.32 (d, 1H), 3.18 (d, 8H), 2.38 (s, 3H), 1.79 (d, 3H).

Example 8: Synthesis of N1-[2-[4-(4-Chloro-2-fluorophenyl)-1-piperazinyl]phenyl]-N4,N4-dimethyl-benzene-1,4-disulfonamide (8)

Step 1: To a 100 mL round-bottom flask was added 30 mL DMF, compound 7a (4.0 g, 28.9 mmol, 1.0 eq), compound 1b (5.5 g, 26.1 mmol, 0.9 eq), K$_2$CO$_3$ (11.9 g, 86.7 mmol, 3.0 q), the temperature was kept at 140° C. for overnight, TLC (PE:EA=10:1, R$_f$=0.4) showed the reaction was having a new point. The reaction was allowed to cool to room temperature and the reaction mixture was poured onto 150 mL ice water, the mixture was stirred for 10 min, extracted with EA (50 mL*3). the combined organic layers were washed with brine and dried over Na$_2$SO$_4$, filtered and concentrated in vacuum. The residue was purified by column chromatography on silica gel to yield the title product 7b (4.1 g, TLC: 95%) as a light-brown solid. Yield: 42.7%.

Step 2: To a 100 mL round-bottom flask was added compound 7b (4.1 g, 12.3 mmol, 1.0 eq) and 40 mL MeOH, sodium borohydride (934 mg, 24.7 mmol, 2.0 eq) was added into the stirred mixture in batches under ice batch (T<10° C.). After stirring at room temperature for 1 h, TLC (PE:EA=10:1, R$_f$=0.05) showed the reaction was completed the reaction mixture was poured onto 80 mL water, the mixture was stirred for 10 min, extracted with EA (80 mL*2). The

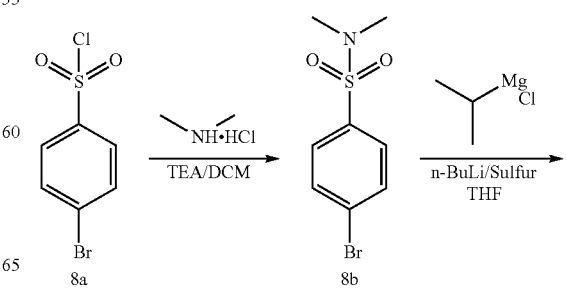

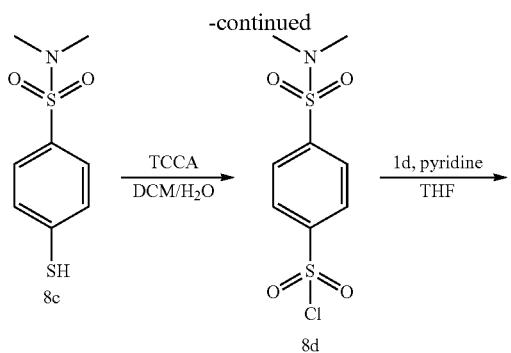

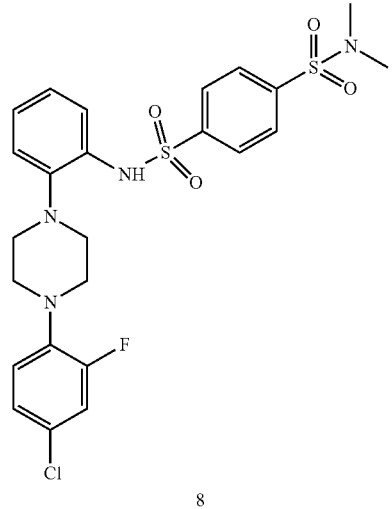

Step 1: To a 3 L three necked flask was added 1000 mL DCM, compound 8a (200 g, 0.78 mol, 1.0 eq) and dimethylamine hydrochloride (83 g, 1.27 mol, 1.02 eq), to the stirred mixture was added TEA (232 g, 2.3 mol, 2.6 eq) under 5-15° C., then the mixture was stirred 2 h at room temperature, TLC (PE:EA=10:1, $R_f$=0.2) showed the reaction was complete. The mixture was poured into water, the aqueous phase extracted with DCM. The organic layer was washed with brine and dried over $Na_2SO_4$, filtered and concentrated under vacuum to yield the title product 8b (200 g) as a white solid, Yield: 97%.

Step 2: To a 500 mL three necked flask was added 57 mL isopropyl magnesium chloride in THF (2M, 0.6 eq), the mixture was controlled under-10° C. in a $N_2$ atmosphere, n-BuLi (76 mL, 0.19 mol, 1.0 eq) was added dropwise into the mixture, then the reaction was keeping the temperature for 15 min, then compound 8b (50 g, 0.19 mol, 1.0 eq) in 500 mL THF was added into the mixture, then the reaction was keeping the temperature for 30 min, sulfur (14 g, 0.23 mol, 2.3 eq) was added into the reaction under −20° C., then the reaction was keeping the temperature for 1 h, TLC (PE:EA=3:1, $R_f$=0.1) showed the reaction was complete and 400 mL HCl aq. was added to the mixture under −10° C., then white solid was precipitation, extracted with EA. The combined organic layer was concentrated under vacuum with low temperature and was purified by column chromatography on silica gel to yield the crude product 8c (1.5 g), Yield: 3.6%.

Step 3: To a 100 mL round-bottom flask was added 50 mL DCM, 10 mL water and concentrated HCl (1.4 g, 2.0 eq), to the stirred mixture was added compound 8c (1.5 g, 1.0 eq), then TCCA (2.0 g, 1.3 eq) was added to the reaction mixture in batches under 0-5° C., the reaction mixture was stirred 30 min at room temperature, TLC (PE:EA=3:1, $R_f$=0.5) showed the reaction was complete. 20 mL MeOH was added to the mixture, the solid particles were filtered from the solution, the filtrate was extracted with DCM. the organic layer was washed with brine and dried over $Na_2SO_4$, filtered and concentrated under vacuum to yield the title product 8d (1.6 g) as a white solid.

Step 4: To a 100 mL round-bottom flask was added 30 mL THF, 2-[4-(4-chloro-2-fluorophenyl) piperazinyl]phenylamine (1d) (0.77 g, 1.0 q), pyridine (0.83 g, 4.2 eq) and compound 8d (0.71 g, 1.0 eq). The reaction was heated to reflux for 15 h. The reaction mixture was concentrated in vacuum and purified by column chromatography on silica gel eluted to afford the title compound 8 (0.15 g). Yield: 13%. MS-ESI: $[M-1]^-$=551.6. $^1$H NMR (300 MHz, CDCl3): δ 8.14 (s, 1H), 8.01 (d, 2H), 7.86 (d, 2H), 7.60 (dd, 1H), 7.24-7.08 (m, 5H), 6.94 (t, 1H), 3.16 (t, 4H), 2.76 (t, 4H), 2.73 (s, 6H).

Example 9: Synthesis of N1-[2-[4-(3-Methoxyphenyl)-1-piperazinyl]phenyl]-N4,N4-dimethylbenzene-1,4-disulfonamide (9)

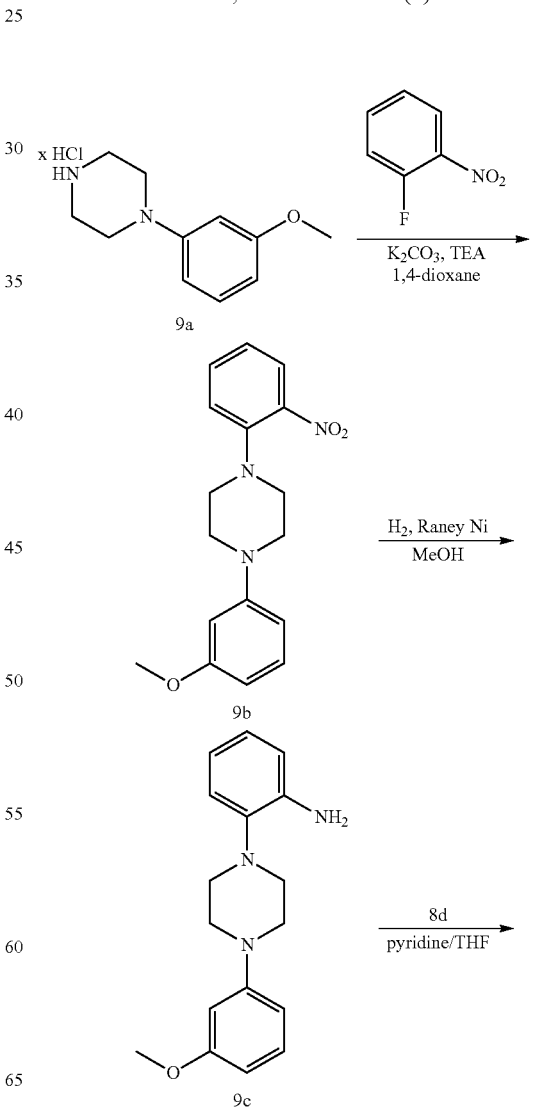

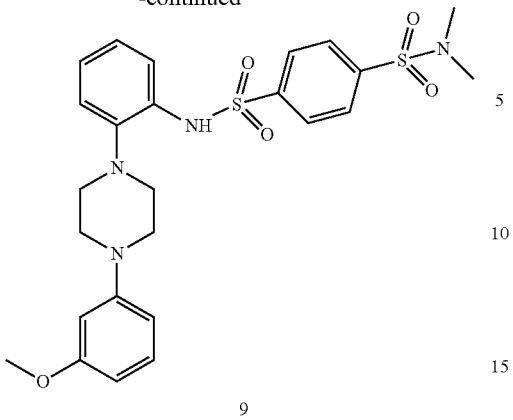

9

Step 1: To a 250 mL round-bottom flask was added 100 mL 1, 4-dioxane, compound 9a (10 g, 1.0 eq), 1-fluoro-2-nitrobenzene (5.8 g, 1.1 eq), K₂CO₃ (13 g, 2.5 eq) and TEA (11 g, 3.0 eq). The mixture was heated to reflux for overnight. The reaction was allowed to cool to room temperature and the reaction mixture was poured into ice water, the mixture was stirred for 10 min, extracted with EA. The combined organic layers were washed with brine and dried over Na₂SO₄, filtered and concentrated in vacuum to afford the title compound 9b (5 g). Yield: 31%.

Step 2: To a 100 mL round-bottom flask was added 50 mL methanol, compound 9b (5 g), Raney-Ni (2.0 g). The reaction was degassed with hydrogen three times and stirred overnight at room temperature. TLC showed the reaction was complete. The reaction mixture was filtered and the filtrate was concentrated in vacuum and purified by column chromatography on silica gel eluted to afford the title compound 9c (1.2 g). Yield: 26%.

Step 3: To a 100 mL round-bottom flask was added 30 ml THF, compound 9c (0.25 g, 1.0 eq), (4-((dimethylamino) sulfonyl) phenyl) chlorosulfone (8d) (0.375 g, 1.5 eq) and pyridine (0.35 g, 5 eq). The reaction was heated to reflux for overnight. The mixture was concentrated in vacuum and the residue was purified by column chromatography on silica gel to afford the title compound 9 (0.16 g), yield: 34%. MS-ESI: [M-1]⁻=529.7. ¹H NMR (300 MHz, CDCl₃): δ 8.25 (s, 1H), 8.10 (d, 2H), 7.95 (d, 2H), 7.71 (d, 1H), 7.38-7.20 (m, 5H), 6.68 (d, 1H), 6.61 (s, 1H), 3.94 (s, 3H), 3.37 (s, 4H), 2.84 (s, 10H).

Example 10: Synthesis of N1-[2-[4-(2-Methoxyphenyl)-1-piperazinyl] phenyl]-N4, N4-dimethylbenzene-1,4-disulfonamide (10)

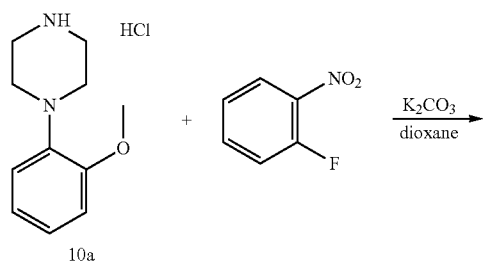

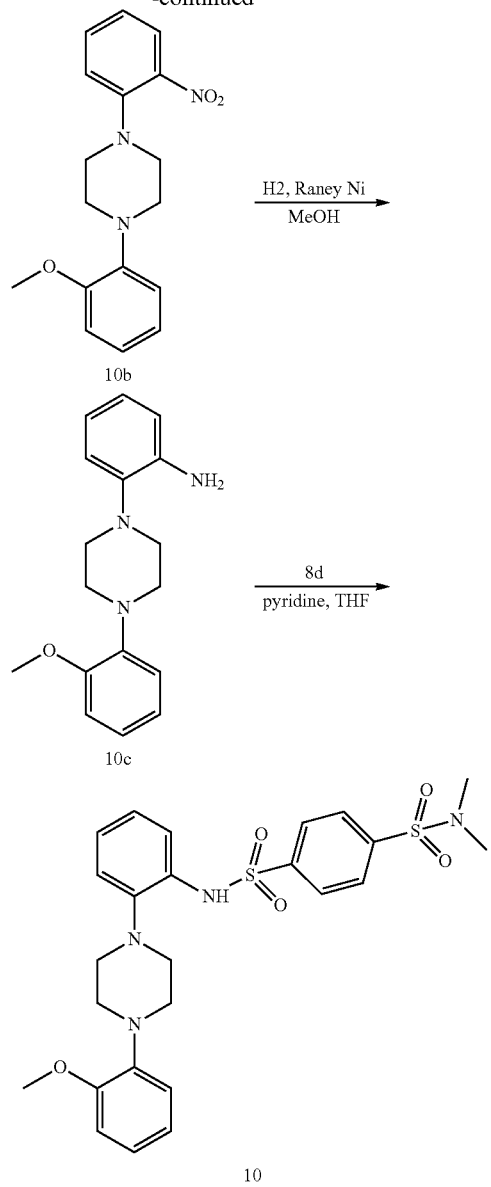

10

Step 1: To a 250 mL round-bottom flask was added 100 mL 1, 4-dioxane, compound 10a (10 g, 52 mmol, 1.0 eq), 1-fluoro-2-nitrobenzene (8 g, 57 mmol, 1.1 eq), K₂CO₃ (18 g, 130 mmol, 2.5 eq), the mixture was heated to reflux for overnight, TLC showed the reaction was complete. The reaction was allowed to cool to room temperature and the reaction mixture was poured onto ice water, the mixture was stirred for 10 min, extracted with EA. The combined organic layers were washed with brine and dried over Na₂SO₄, filtered and concentrated in vacuum to yield the title product 10b (8 g). Yield: 50%.

Step 2: To a 100 mL round-bottom flask was added 50 mL methanol. To the stirred mixture was added compound 10b (8 g), Raney-Ni (2.0 g), the reaction was stirred overnight at room temperature. TLC showed the reaction was complete. The reaction mixture was filtered and the filtrate was concentrated in vacuum and purified by column chromatography on silica gel eluted to obtained the title product 10c (2 g). Yield: 27%.

Step 3: To a 50 mL round-bottom flask was added 5 mL pyridine, compound 10c (0.25 g, 1.0 eq), (4-((dimethylamino) sulfonyl) phenyl) chlorosulfone (8d) (0.375 g, 1.5 eq), pyridine (0.35 g, 5.0 eq), THF 50 mL, the reaction was heated to reflux for overnight. TLC showed the reaction was completed, the mixture was concentrated in vacuum and the residue was purified by column chromatography on silica gel to yield the title product 10 (0.16 g, UPLC: 91.8%), yield: 34%. MS-ESI: [M−1]⁻=529.7. ¹H NMR (300 MHz, CDCl3): δ 8.25 (s, 1H), 8.01 (d, 2H), 7.85 (d, 2H), 7.64 (d, 1H), 7.25-6.91 (m, 7H), 3.91 (s, 3H), 3.17 (s, 4H), 2.73 (s, 10H).

Example 11: Synthesis of N1, N1-Dimethyl-N4-[2-(4-phenyl-1-piperazinyl) phenyl] benzene-1,4-disulfonamide (11)

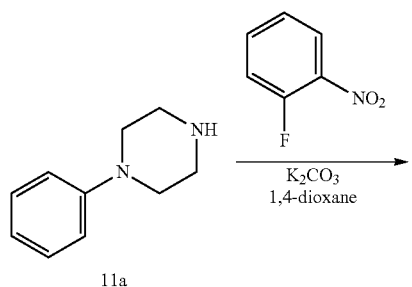

11a

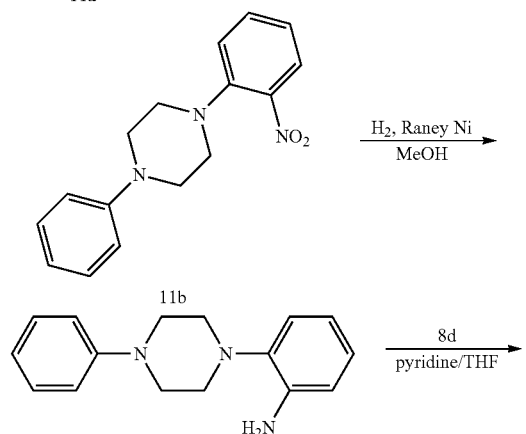

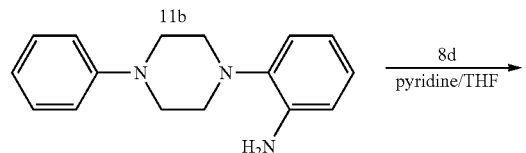

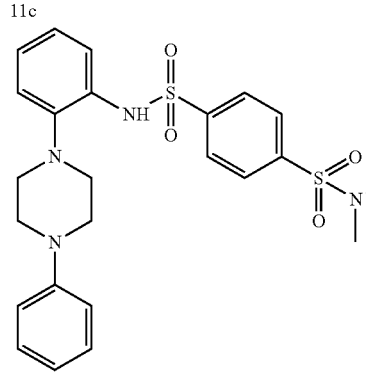

11

Step 1: To a 250 mL round-bottom flask was added 100 mL 1, 4-dioxane, compound 11a (10 g, 1.0 eq), 1-fluoro-2-nitrobenzene (8.6 g, 1.0 eq) and K₂CO₃ (17 g, 2.0 eq). The mixture was heated to reflux for overnight, TLC showed the reaction was complete. The reaction was allowed to cool to room temperature and the reaction mixture was poured into ice water, the mixture was stirred for 10 min, extracted with EA (100 ml*3). The combined organic layers were washed with brine and dried over Na2SO4, filtered and concentrated in vacuum to afford the title compound 11b (15 g). Yield: 86.1%.

Step 2: To a 250 mL round-bottom flask was added 80 mL methanol, compound 11b (15 g), Raney-Ni (3.0 g). The reaction was degassed with hydrogen three times and stirred overnight at room temperature. TLC showed the reaction was complete. The reaction mixture was filtered and the filtrate was concentrated in vacuum to afford the title compound 11c (13 g). Yield: 96.9%.

Step 3: To a 100 mL round-bottom flask was added 50 ml THF, compound 11c (0.4 g, 1.0 eq), (4-((dimethylamino) sulfonyl) phenyl) chlorosulfone (8d) (0.6 g, 1.5 eq) and 10 mL pyridine. The reaction was heated to 60° C. for overnight. The mixture was concentrated in vacuum and the residue was purified by column chromatography on silica gel to afford the title compound 11 (350 mg), yield: 44.4%. MS-ESI: [M+1]⁻=501.8. ¹H NMR (300 MHz, CDCl3): δ 8.15 (s, 1H), 8.02 (d, 2H), 7.87 (d, 2H), 7.61 (d, 1H), 7.44-7.33 (m, 2H), 7.25-6.96 (m, 6H), 3.32 (s, 4H), 2.74 (s, 10H).

Example 12: Synthesis of N-[2-[4-(4-Chloro-2-fluorophenyl)-1-piperazinyl]phenyl]-4-(difluoromethyl) benzenesulfonamide (12)

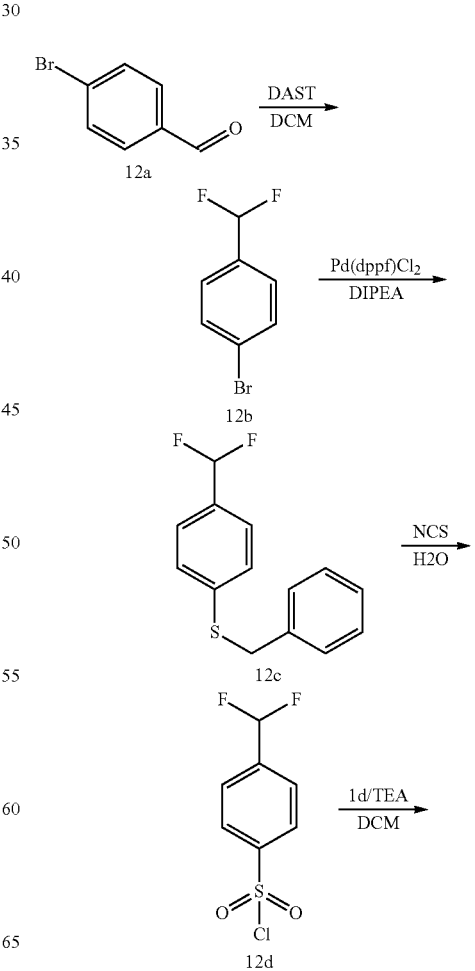

43
-continued

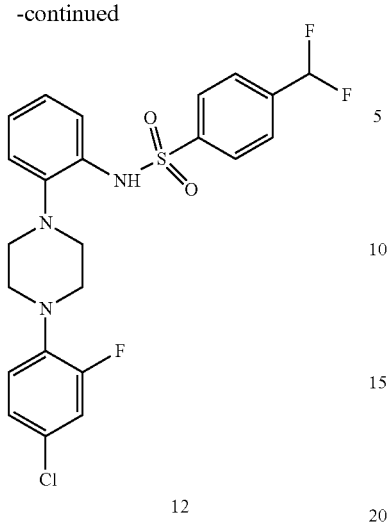

12

Step 1: To a 1 L round-bottom flask was added 500 mL DCM, compound 12a (100 g, 0.54 mol, 1.0 q), and DAST (125 g, 0.7 mol, 1.3 eq). The reaction was heated to reflux for 1 h and then stirred at rt for 15 h. TLC showed the reaction was completed. The reaction mixture was poured into Saturated NaHCO$_3$(T<10° C.). The DCM layer was dried, concentrated in vacuum and purified by column chromatography on silica gel eluted with PE to afford the compound 12b (90 g) as a colorless oil. Yield: 81%.

Step 2: To a 250 mL round-bottom flask was added 150 mL toluene, compound 12b (19 g, 0.09 mol, 1.0 q), Benzyl mercaptan (12.5 g, 0.1 mol, 1.1 eq), DIPEA (23.7 g, 0.18 mol, 2.0 eq), [1,1'-bis(diphenylphosphino)ferrocene]dichloropalladium(II) complex with dichloromethane (3.7 g, 0.005 mol, 0.05 eq) and 4,5-bis(diphenylphosphino)-9,9-dimethylxanthene (5.3 g, 0.009 mol, 0.1 eq). The reaction was heated to reflux for 15 h. The reaction mixture was concentrated in vacuum and purified by column chromatography on silica gel eluted to afford the title compound 12c (15 g). Yield: 65%.

Step 3: To a 250 mL round-bottom flask was added 80 mL acetic acid glacial, 25 mL H2O, compound 12c (3 g, 1.0 q) and NCS (6.4 g, 4.0 eq). The reaction was stirred at 15° C. for 1 h. The reaction mixture was concentrated in vacuum. The residue was added DCM, adjusted the pH>7 with Saturated NaHCO3. The DCM layer was dried, concentrated in vacuum to afford the compound 12d.

Step 4: To a 100 mL round-bottom flask was added 20 mL DCM, compound 12d (2.0 eq), 2-[4-(4-chloro-2-fluorophenyl) piperazinyl]phenylamine (1d) (0.2 g, 1.0 eq) and TEA (3.0 eq). The reaction was heated to reflux for 15 h. The reaction mixture was concentrated in vacuum, added water, extracted with DCM. The DCM layer was dried, concentrated in vacuum and purified by column chromatography on silica gel eluted to afford the title compound 12 (0.05 g) as a white solid. Yield: 15%. MS-ESI: [M−1]$^-$=494.6. $^1$H NMR (300 MHz, CDCl3): δ 8.08 (s, 1H), 7.95 (d, 2H), 7.68-7.62 (m, 3H), 7.22-7.08 (m, 5H), 6.94 (t, 1H), 6.67 (t, 1H), 3.15 (t, 4H), 2.74 (t, 4H).

44

Example 13: Synthesis of Example 13: N-[2-[4-(4-Chloro-2-fluorophenyl)-2-methyl-1-piperazinyl]phenyl]-4-methylbenzenesulfonamide (13)

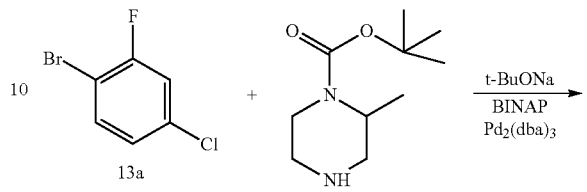

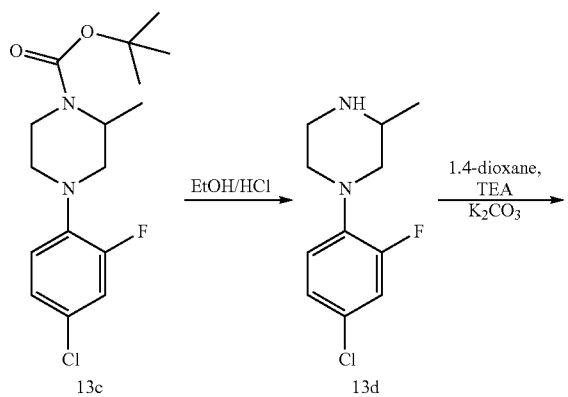

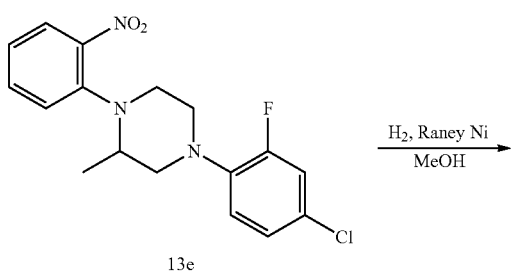

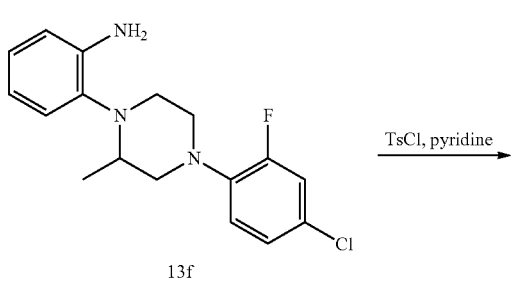

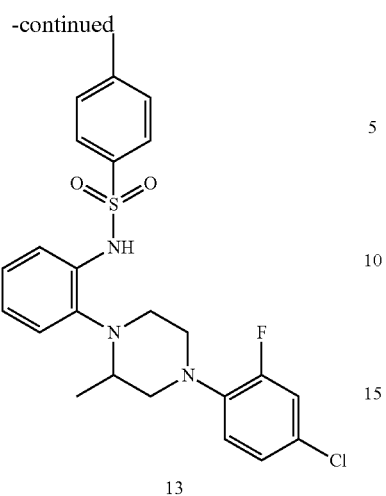

13

Step 1: To a 100 mL three-necked flask was added 20 mL toluene and compound 13a (3 g, 0.014 mol, 1.0 eq), compound 13b (4.3 g, 0.022 mol, 1.5 eq) and t-BuONa (2.064 g, 0.022 mol, 1.5 eq). The reaction was heated to 80° C. with nitrogen. Then BINAP (0.3 g, 0.42 mmol, 0.03 eq) and Pd$_2$(dba)$_3$.CHCl$_3$ (0.15 g, 0.14 mmol, 0.001 eq) was added to the stirred mixture. The reaction was heated to reflux for 18 h. The solution was cooled, concentrated and extracted with 30 EA from 10 mL water. The organic layer was washed with brine, dried, concentrated in vacuum and purified by column chromatography on silica gel eluted with PE:EA=10:1 to afford the compound 13c (4 g, HPLC: 98%) as a white solid. Yield: 86%.

Step 2: To a 1 L round-bottom flask was added compound 13c (4 g, 0.205 mol, 1.0 eq) and 20 mL EtOH. 20 mL HCl/EtOH (33%) was dropped into the stirred mixture (T<10° C.). After stirring at room temperature for 2 h, the solution was concentrated. 10 mL water was added. Then 4N NaOH was dropped into the stirred mixture to adjust pH=10 (T<10° C.) and extracted with DCM (20 mL*2). The organic layer was dried and concentrated in vacuum to afford the compound 13d (1.5 g, HPLC: 92%) as a white solid. Yield: 32%.

Step 3: To a 250 mL round-bottom flask was added 1.4-dioxane 10 mL, compound 13d (1.5 g, 0.011 mol, 1.0 eq) and TEA (3.19 g, 0.036 mol, 3 eq) was dropped into the stirred mixture at room temperature for 15 min. And potassium carbonate (3.64 g, 0.0266 mol, 2.5 eq) and compound 1-fluoro-2-nitrobenzene (1.5 g, 0.0095 mol, 0.9 eq) was dropped into the stirred mixture and refluxed for 3 h. This reaction was added water 200 mL and extracted with EA (5 mL*3), the organic solution was dried over sodium sulfate, filtered, and concentrated to afford the title compound 13e (2 g, HPLC: 98%) Yield: 56.8%

Step 4: To a 50 mL round-bottom flask was added methanol 20 mL, compound 13e (2 g, 0.0056 mol, 1.0 eq), Raney-Nickel catalyst (0.5 g) was dropped into the stirred mixture at room temperature for overnight. The solution was filtered, and concentrated to afford the title compound 13f (1.2 g, HPLC: 94%) Yield: 70%

Step 5: To a 50 mL round-bottom flask was added pyridine 10 mL, compound 13f (1 g, 3.27 mmol, 1.0 eq) and TsCl (0.8 g, 4.2 mmol, 1.3 eq) was dropped into the stirred mixture at room temperature for 2 h. The solution was concentrated and subjected to silica gel eluted to afford the title compound 13 (54 mg, HPLC: 96%) as a white solid. Yield: 4%. [M−1]$^-$=472.4. $^1$H NMR (400 MHz, DMSO): δ 8.83 (s, 1H), 7.71 (d, 2H), 7.50 (d, 1H), 7.39-7.35 (m, 4H), 7.25 (s, 1H), 7.19-7.05 (m, 3H), 3.29 (d, 1H), 3.11 (d, 2H), 2.99 (t, 1H), 2.81-2.64 (m, 3H), 2.33 (s, 3H), 2.10 (d, 1H), 0.57 (d, 3H)

Example 14: Synthesis of N-[2-[4-(4-Chloro-2-fluorophenyl)-1-piperazinyl]phenyl]-4-methoxybenzenesulfonamide (14)

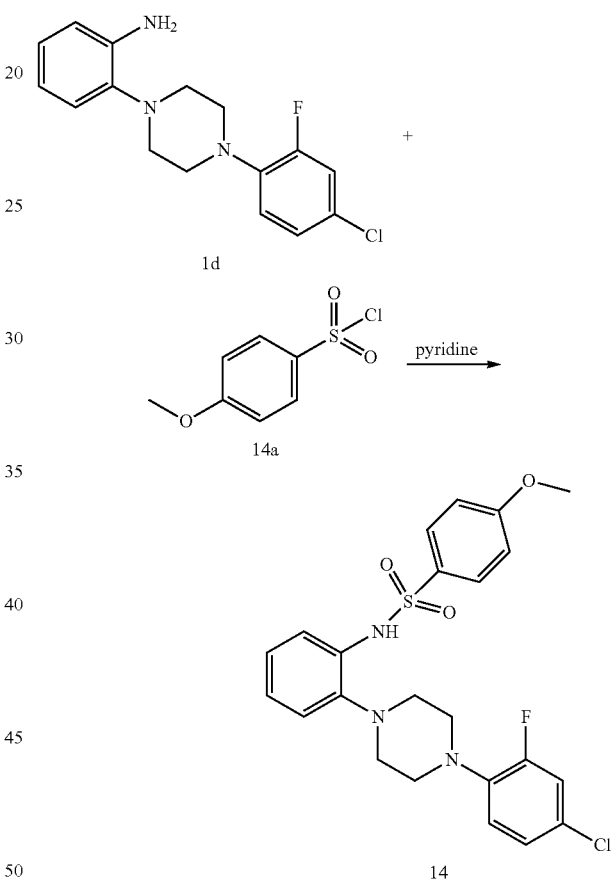

Step 1: To a 50 mL round-bottom flask was added 6 mL pyridine. To the stirred mixture was added compound 1d (305 mg, 1.0 mmol, 1.0 eq), compound 14a (207 mg, 1.0 mmol, 1.0 eq). The reaction was stirred at room temperate overnight. TLC (PE:EA=5:1, R$_f$=0.3) showed the compound 1d was not consumed completely. The reaction mixture was concentrated in vacuum and purified by column chromatography on silica gel eluted with PE:EA=5:1 to yield the title product compound 14 (80 mg, HPLC: 94.8%) as an off-white solid. Yield: 16.8%.

MS-ESI: [M+H]$^+$=476.7. $^1$H NMR (400 MHz, CDCl3): δ 8.12 (s, 1H), 7.79 (d, 2H), 7.62 (d, 1H), 7.19 (dd, 2H), 7.15-7.05 (m, 3H), 7.00 (t, 1H), 6.91 (d, 2H), 3.84 (s, 3H), 3.21 (s, 4H), 2.83 (s, 4H).

Example 15: Synthesis of N-[2-[4-(4-Chloro-2-fluorophenyl)-1-piperazinyl]phenyl]-2-methylbenzenesulfonamide (15)

Example 16: N-[2-[4-(4-Chlorophenyl)-1-piperazinyl]phenyl]-4-methylbenzenesulfonamide (16)

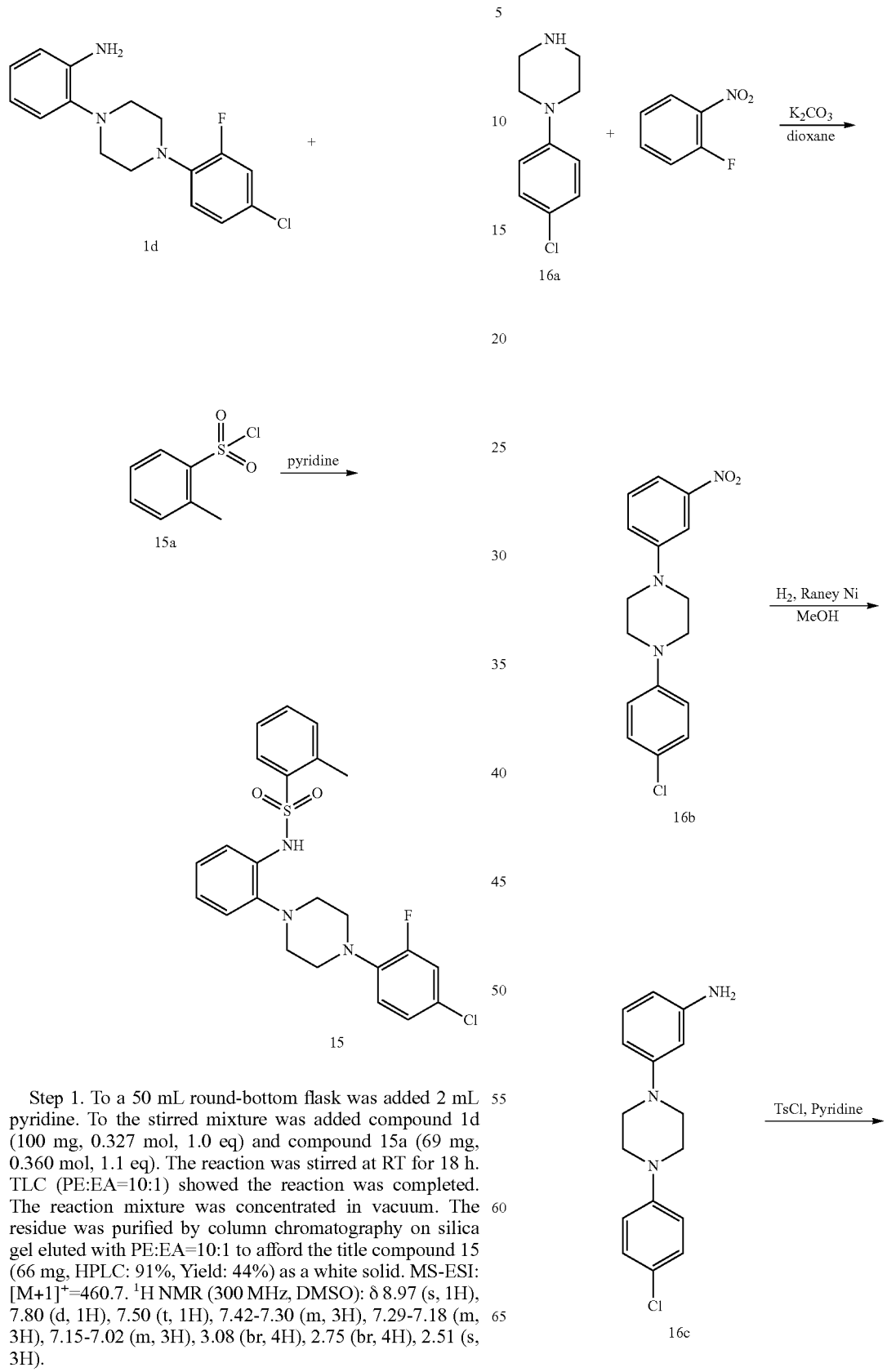

Step 1. To a 50 mL round-bottom flask was added 2 mL pyridine. To the stirred mixture was added compound 1d (100 mg, 0.327 mol, 1.0 eq) and compound 15a (69 mg, 0.360 mol, 1.1 eq). The reaction was stirred at RT for 18 h. TLC (PE:EA=10:1) showed the reaction was completed. The reaction mixture was concentrated in vacuum. The residue was purified by column chromatography on silica gel eluted with PE:EA=10:1 to afford the title compound 15 (66 mg, HPLC: 91%, Yield: 44%) as a white solid. MS-ESI: [M+1]$^+$=460.7. $^1$H NMR (300 MHz, DMSO): δ 8.97 (s, 1H), 7.80 (d, 1H), 7.50 (t, 1H), 7.42-7.30 (m, 3H), 7.29-7.18 (m, 3H), 7.15-7.02 (m, 3H), 3.08 (br, 4H), 2.75 (br, 4H), 2.51 (s, 3H).

Example 17: Synthesis of 4-Methyl-N-[2-[4-(p-tolyl)-1-piperazinyl] phenyl]benzenesulfonamide (17)

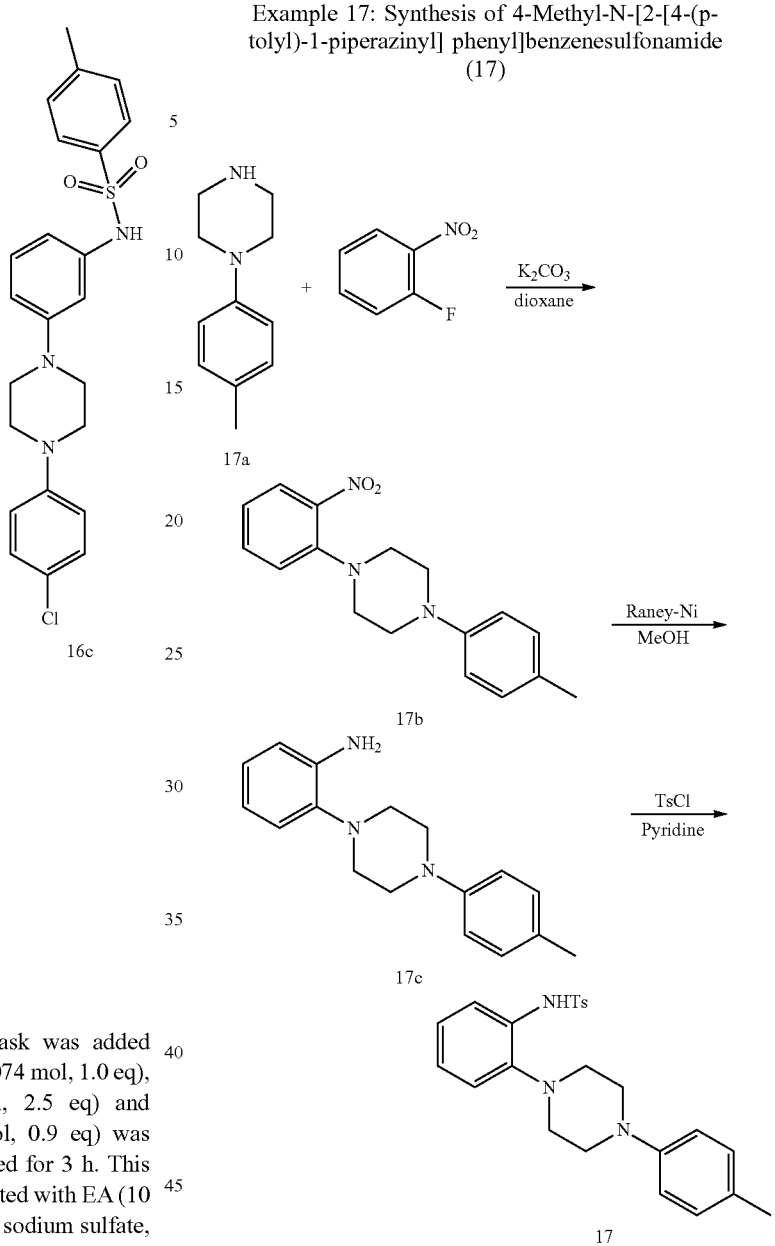

Step 1: To a 100 mL round-bottom flask was added 1,4-dioxane 20 mL, compound 16a (2 g, 0.0074 mol, 1.0 eq), potassium carbonate (2.48 g, 0.018 mol, 2.5 eq) and 1-fluoro-2-nitrobenzene (0.94 g, 0.007 mol, 0.9 eq) was dropped into the stirred mixture and refluxed for 3 h. This reaction was added water 200 mL and extracted with EA (10 mL*3), The organic solution was dried over sodium sulfate, filtered, and concentrated to afford the title compound 16b (3.1 g, HPLC: 91%)

Step 2: To a 100 mL round-bottom flask was added methanol 20 mL, compound 16b (2.93 g, 0.0094 mol, 1.0 eq), Raney-Nickel catalyst (1 g) was dropped into the stirred mixture at room temperature for overnight. The solution was filtered, and concentrated to afford the title compound 16c (2.5 g, HPLC: 90%) Yield: 96%

Step 3: To a 50 mL round-bottom flask was added pyridine 20 mL, compound 16c (200 mg, 1.06 mmol, 1.0 eq) and TsCl (242 mg, 1.27 mmol, 1.2 eq) was dropped into the stirred mixture at room temperature for 2 h. The solution was concentrated and subjected to silica gel eluted to afford the title compound 16 (72 mg, HPLC: 96%). Yield: 24%. [M+1]$^+$=442.0. $^1$H NMR (400 MHz, CDCl$_3$): δ 7.99 (s, 1H), 7.73 (d, 2H), 7.63 (dd, 1H), 7.34-7.29 (m, 1H), 7.28-7.22 (m, 3H), 7.21-7.13 (m, 2H), 7.12-7.05 (m, 1H), 7.05-6.85 (m, 2H), 3.40-3.15 (m, 4H), 2.90-2.60 (m, 4H), 2.40 (s, 3H).

Step 1: To a 100 mL round-bottom flask was added 15 mL 1,4-dioxane, 1-fluoro-2-nitrobenzene (1.27 g, 9.0 mmol, 0.9 eq), compound 17a (1.76 g, 10 mmol, 1.0 eq), K$_2$CO$_3$ (3.45 g, 25 mmol, 2.5 q), the temperature was heated to reflux for overnight, TLC (PE:EA=10:1, R$_f$=0.4) showed the reaction was completed. The reaction was allowed to cool to room temperature and the reaction mixture was poured onto 50 mL ice water, the mixture was stirred for 10 min, extracted with EA (30 mL*3). The combined organic layers were washed with brine and dried over Na$_2$SO$_4$, filtered and concentrated in vacuum. The residue was beat with PE (5 mL) to yield the title product 17b (2.5 g, HPLC: 96.9%) as a yellow solid. Yield: 84.1%.

Step 2: To a 100 mL round-bottom flask was added 50 mL methanol. To the stirred mixture was added compound 17b (2.4 g, 8.08 mmol, 1.0 eq), Raney-Ni (0.5 g, 20% wt) and hydrogen. The reaction was stirred overnight at 40° C. TLC (PE:EA=10:1, R$_f$=0.45) showed the reaction was complete.

The reaction mixture was filtered and the filtrate was concentrated in vacuum and purified by column chromatography on silica gel eluted with PE:EA=20:1 to yield the title product 17c (1.0 g, HPLC: 88%). Yield: 47.6%.

Step 3: To a 50 mL round-bottom flask was added 6 mL pyridine. To the stirred mixture was added compound 17c (300 mg, 1.12 mmol, 1.0 eq), TsCl (234.8 mg, 1.23 mmol, 1.1 eq). The reaction was stirred at room temperate overnight. TLC (PE:EA=10:1, $R_f$=0.1) showed the 17c was not consumed completely. The reaction mixture was concentrated in vacuum and purified by column chromatography on silica gel eluted with PE:EA=30:1 to yield the title product 17 (116 mg, HPLC: 93%) as a yellow solid, Yield: 24.6%. MS-ESI: $[M+H]^+$=422.4. $^1$H NMR (400 MHz, CDCl3): δ 8.01 (s, 1H), 7.72 (dd, 2H), 7.65 (dd, 1H), 7.24 (d, 2H), 7.22-7.12 (m, 4H), 7.11-6.73 (m, 3H), 3.23 (br, 4H), 2.72 (br, 4H), 2.39 (s, 3H), 2.33 (s, 3H).

Example 18: Synthesis of N-[2-[4-(4-Methoxyphenyl)-1-piperazinyl] phenyl]-4-methylbenzenesulfonamide (18)

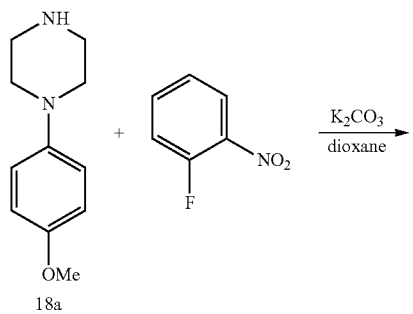

18a

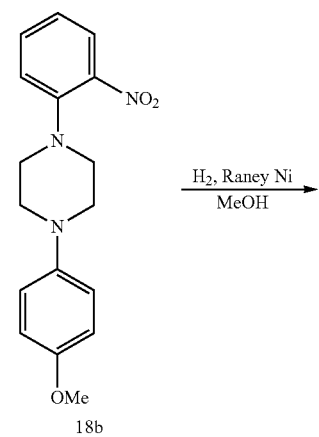

18b

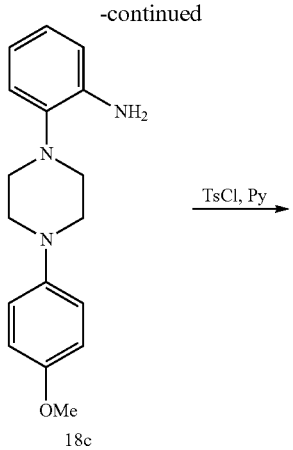

18c

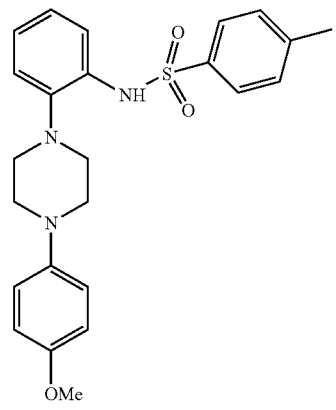

18

Step 1: To a 100 mL round-bottom flask was added 20 mL 1,4-Dioxane, compound 18a (2 g, 10.4 mmol, 1.0 eq), 1-fluoro-2-nitrobenzene (1.32 g, 9.36 mmol, 0.9 eq) and K$_2$CO$_3$ (3.59 g, 26.0 mmol, 2.5 eq). The reaction was heated to reflux for 18 h with nitrogen. TLC (PE:EA=3:1) showed the reaction was completed. The reaction mixture was poured into 100 mL water and extracted with EA (20 mL*2). The organic layer was dried, concentrated in vacuum to afford the compound 18b (3.1 g, HPLC: 91%, Yield: >100%) as a yellow solid.

Step 2: To a 100 mL round-bottom flask was added 30 mL MeOH, compound 18b (2.93 g, 9.36 mmol, 1.0 eq) and Raney Ni (1 g, 34 wt %). The reaction was degassed with hydrogen three times and stirred at 45° C. for 15 h. TLC (PE:EA=3:1) showed the reaction was completed. The reaction mixture was filtered and washed with DCM. The filtrate was concentrated in vacuum. The residue was washed with tert-butyl methyl ether to afford the title compound 18c (2.5 g, HPLC: 90% Yield: 96%) as a brown solid.

Step 3: To a 25 mL round-bottom flask was added 3 mL Pyridine, compound 18c (300 mg, 1.06 mmol, 1.0 eq) and TsCl (242 mg, 1.27 mmol, 1.2 eq). The reaction was stirred at RT for 18 h. The reaction mixture was concentrated in vacuum and purified by column chromatography on silica gel eluted with PE:EA=10:1 to afford the title compound 18 (80 mg, HPLC: 90%, Yield: 17.3%). MS-ESI: $[M+1]^+$=438.1. $^1$H NMR (400 MHz, CDCl$_3$): δ 8.01 (s, 1H), 7.72 (d, 2H), 7.65 (d, 1H), 7.24 (d, 2H), 7.21-7.12 (m, 2H), 7.08 (t, 1H), 7.04-6.79 (m, 4H), 3.83 (s, 3H), 3.20 (br, 4H), 2.76 (br, 4H), 2.39 (s, 3H).

Example 19: Synthesis of N-[2-[4-(4-Chloro-2-fluorophenyl)-1-piperazinyl]phenyl]-4-cyanobenzenesulfonamide (19)

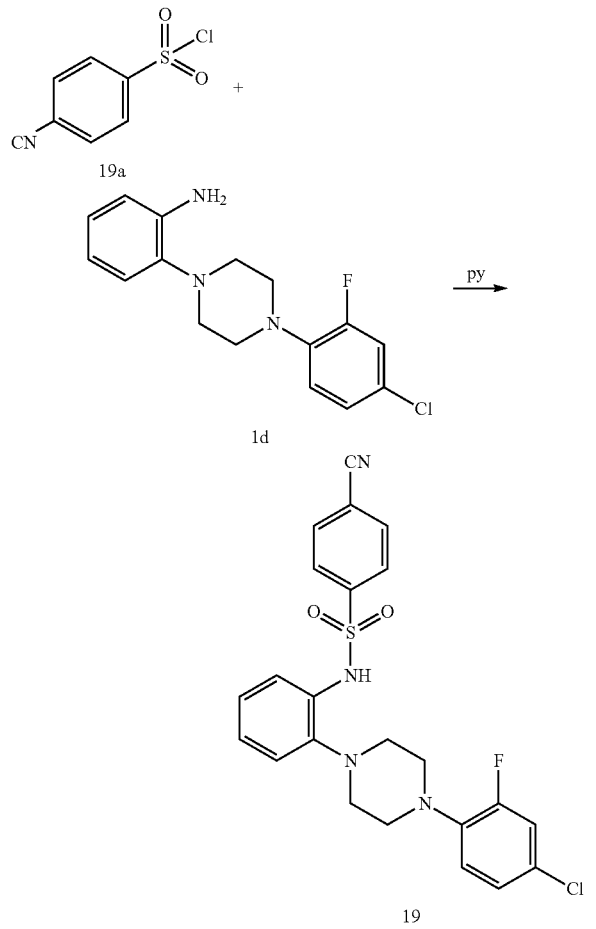

Step 1: To a 50 mL round-bottom flask was added 6 mL pyridine. To the stirred mixture was added compound 1d (305.7 mg, 1.0 mmol, 1.0 eq), compound 19a (241.8 mg, 1.2 mmol, 1.2 eq). The reaction was stirred at room temperate for 2 h. TLC (PE:EA=10:1, $R_f$=0.1) showed the reaction was having a new point, but compound 1d was not consumed completely. The reaction mixture was concentrated in vacuum and purified by column chromatography on silica gel eluted with PE:EA=20:1 to yield the title product 19 (220 mg, HPLC: 94.9%) as a white solid. Yield: 46.8%. MS-ESI: $[M+H]^+$=471.0. $^1$H NMR (400 MHz, CDCl3): δ 8.36 (br, 1H), 8.00 (d, 2H), 7.78 (d, 2H), 7.55 (d, 1H), 7.27-7.05 (m, 5H), 6.98 (t, 1H), 3.24 (br, 4H), 2.88 (br, 4H).

BIOLOGICAL DATA

Example B1: Mammalian Whole-Cell Electrophysiology

HEK293T, Cos-1 and CHO cells were used for the heterologous expression experiments and were transfected using Lipofectamine 2000 (Invitrogen). The pipette solution contained 147 mM Cs, 120 mM methane-sulphonate, 4 mM NaCl, 10 mM EGTA, 2 mM Na2-ATP, 2 mM MgCl$_2$ and 20 mM HEPES (pH 7.2; free [Ca2+]i<10 nM). The standard extracellular bath solution (modified Tyrode's solution) contained 153 mM NaCl, 5 mM KCl, 2 mM CaCl$_2$, 1 mM MgCl$_2$, 20 mM HEPES and 10 mM glucose (pH 7.4). The 'Low pH Tyrode' solution contained 150 mM Na-gluconate, 5 mM KCl, 2 mM CaCl$_2$, 1 mM MgCl$_2$, 10 mM glucose, 10 mM HEPES and 10 mM MES (pH 4.6). All bath solutions were applied via a perfusion system to achieve a complete solution exchange within a few seconds. Data were collected using an Axopatch 2A patch clamp amplifier, Digidata 1440 and pClamp 10.0 software (Axon Instruments). Whole-cell currents were digitized at 10 kHz and filtered at 2 kHz. All experiments were conducted at room temperature (21-23° C.), and all recordings were analysed with pClamp 10.0 and Origin 8.0 (OriginLab, Northampton, Mass., USA).

Example B2: Endolysosomal Electrophysiology

Endolysosomal electrophysiology was performed in isolated endolysosomes using a modified patch-clamp method. Briefly, cells were treated with 1 μM vacuolin-1 for 2-5 h to increase the size of endosomes and lysosomes. Whole-endolysosome recordings were performed on isolated enlarged LELs. The bath (internal/cytoplasmic) solution contained 140 mM K-gluconate, 4 mM NaCl, 1 mM EGTA, 2 mM Na2-ATP, 2 mM MgCl$_2$, 0.39 mM CaCl$_2$, 0.2 mM GTP and 10 mM HEPES (pH adjusted with KOH to 7.2; free [Ca$^{2+}$+]i~100 nM based on the Maxchelator software (http://maxchelator.stanford.edu/)). The pipette (luminal) solution consisted of a 'Low pH Tyrode's solution with 145 mM NaCl, 5 mM KCl, 2 mM CaCl$_2$, 1 mM MgCl$_2$, 10 mM HEPES, 10 mM MES and 10 mM glucose (pH 4.6).

In this electrophysiology assays, Examples 1 and 8 are >10× more potent than ML-SA1.

Example B3: Lysosomal Ca$^{2+}$ Imaging

GCaMP3-ML1 expression was induced in Tet-On HEK-GCaMP3-ML1 cells 20-24 h prior to experiments using 0.01 μg/mL doxycycline. GCaMP3-ML1 fluorescence was monitored at an excitation wavelength of 470 nm ($F_{470}$) using a EasyRatio Pro system (PTI). Cells were bathed in Tyrode's solution containing 145 mM NaCl, 5 mM KCl, 2 mM CaCl$_2$, 1 mM MgCl$_2$, 10 mM Glucose, and 20 mM Hepes (pH 7.4). Lysosomal Ca$^{2+}$ release was measured in a zero Ca$^{2+}$ solution containing 145 mM NaCl, 5 mM KCl, 3 mM MgCl$_2$, 10 mM glucose, 1 mM EGTA, and 20 mM HEPES (pH 7.4). Ca$^{2+}$ concentration in the nominally free Ca$^{2+}$ solution is estimated to be 1-10 μM. With 1 mM EGTA, the free Ca$^{2+}$ concentration is estimated to be <10 nM based on the Maxchelator software (http://maxchelator.stanford.edu/). Experiments were carried out 0.5 to 6 hrs after plating.

In this calcium imaging assay, Examples 1 and 8 are >10× more potent than ML-SA1.

Example B4: TFEB Nuclear Translocation Assay

TFEB is a transcription factor and master regulator of lysosome biogenesis and autophagy. TFEB activation is shown to induce cellular clearance in a variety of LSDs and common neurodegenerative diseases. Hence TFEB activity can be used to evaluate the cellular efficacy of TRPML agonists.

Intracellular TFEB localization is determined either by immunofluorescence in Hela cells or by fluorescent microscopy in Hela cells stably expressing TFEB-GFP. Detailed procedures are as follows.

Cells grown on cover slips were treated with TRPML1 agonist(s) or antagonist(s) for indicated time period and then fixed with 4% paraformaldehyde for 15 minutes at room temperature. For immunofluorescent detection of endogenous TFEB, cells were permeabilized with 0.3% Triton X-100, blocked with 1% bovine serum albumin (BSA) in phosphate buffered saline (PBS) and then immunostained with anti-TFEB antibody (1:200; Cell Signaling Technology) at 4° C. for overnight. The stained cells were then incubated with secondary antibodies conjugated to Alexa Fluor 568 or 488 (ThermoFisher) for 1 h, then 4',6-diamidino-2-phenylindole (DAPI) for 15 minutes (to stain the cell nucleus) and mounted on glass slides with Fluoromount-G (Southern Biotech) for observation. Images were acquired with a Spinning-Disk Confocal microscope (Olympus) and Metamorph software (Molecular Devices).

Average ratios of nuclear versus cytosolic TFEB fluorescence intensity (>50 randomly-selected cells per experiment) were determined with ImageJ software (NIH).

Figure 2:
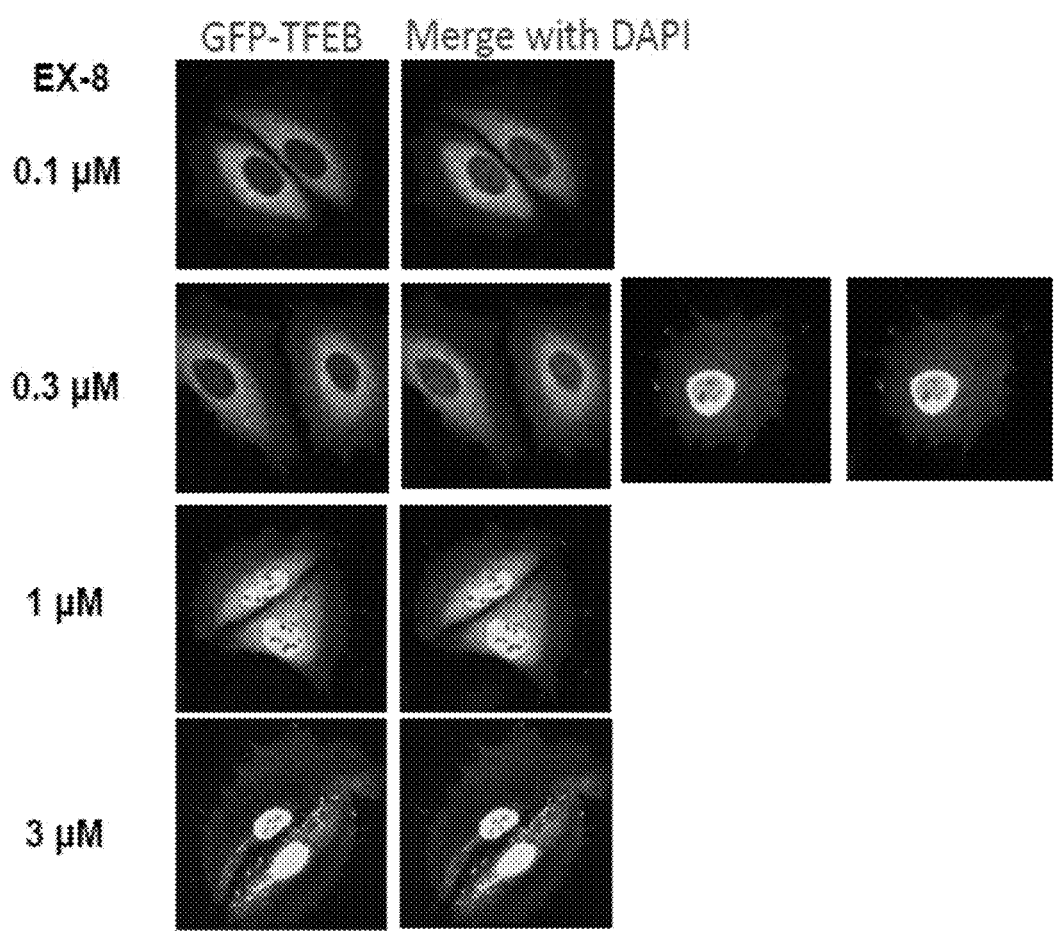
FIG. 2 shows certain experimental results in connection with Example 8.

In HEK293 cells stably expressing GFP-TFEB (TFEB stable cells), we found that application of TRPML1 agonists, for example, example 8, was sufficient to induce TFEB-nuclear translocation (nuclear to cytosol ratio increased in a dose-dependent manner as shown in FIG. 2.

Example B5: UV Treatment and ROS Staining

HaCat cells (a human keratinocyte cell line) at a confluency of around 50% were incubated with 20 M H2DCFDA (Sigma) in the culture media without FBS at 37° C. for 30 min, and then washed twice with phosphate buffered saline (PBS, pH 7.4) before being exposed to UV. A CL-1000 UV Crosslinker (UVP) is used to shed 600 J/m² of UV light (254 nm) on the HaCat cells in all experiments. Fluorescent images were obtained right after UV exposure, via an Olympus IX73 microscopy (Olympus) and Metamorph software (Molecular Devices).

Figure 3:
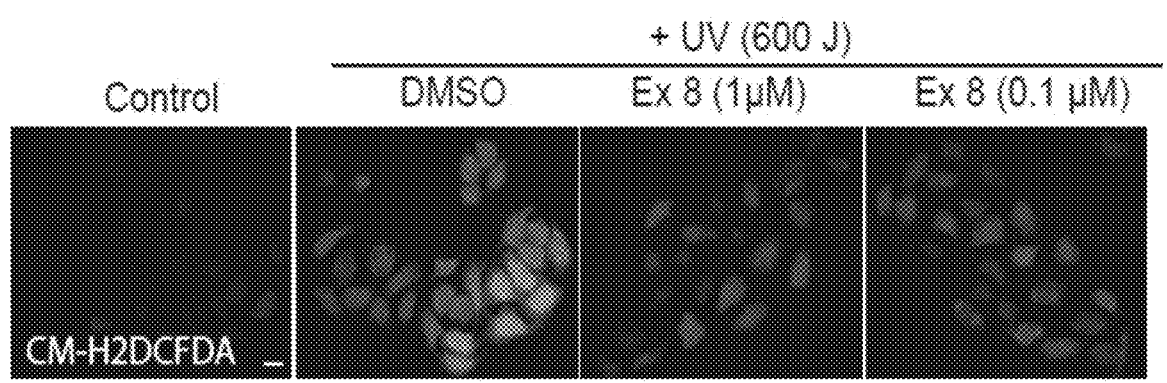
FIG. 3 shows certain experimental results in connection with Example 8.

In this assay example 8 significantly reduced UV induced ROS as shown in FIG. 3.

What is claimed:

1. A compound of formula I:

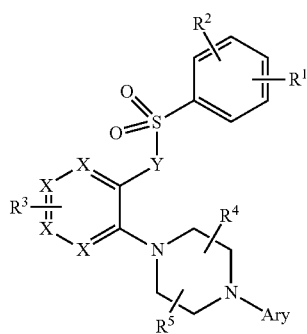

or a salt thereof; or a prodrug, or a salt of a prodrug thereof; or a hydrate, solvate, or polymorph thereof, wherein:
each X is independently $CR_6$ or N;
Y is $NR_7$ or $CR_8R_9$;
Ary is phenyl or heteroaryl optionally substituted with 1, 2, or 3 substituents independently selected from $C_{1-3}$ alkyl, halo, OH, CN, OR, NHR, NRR', N(R)C(=O)R', N(R)C(=O)(O)R', OC(=O)NRR', C(=O)R, C(=O)NRR', N(R)S(O)2R', S(O)2R, and S(O)2NRR';
$R_1$, $R_2$, $R_3$, $R_4$, $R_5$, $R_6$, $R_7$, $R_8$, $R_9$ each are independently H, $C_{1-3}$ alkyl, halogen, oxo, OH, CN, OR, NHR, NRR', N(R)C(=O)R', N(R)C(=O)(O)R', OC(=O)NRR', C(=O)R, C(=O)NRR', N(R)S(O)2R', S(O)2R, or S(O)2NRR';
R, R' each are independently H, or $C_{1-3}$ alkyl;
and wherein said compound is other than:

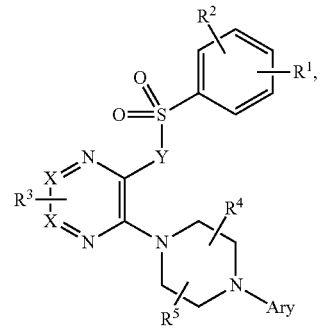

wherein X, Y, Ary, $R_1$, $R_2$, $R_3$, $R_4$, and $R_5$ are as defined above.

2. A compound according to claim 1 wherein Ary is phenyl optionally substituted with 1, 2, or 3 substituents independently selected from $C_{1-3}$ alkyl, halo, OH, CN, OR, NHR, NRR', N(R)C(=O)R', N(R)C(=O)(O)R', OC(=O)NRR', C(=O)R, C(=O)NRR', N(R)S(O)2R', S(O)2R, and S(O)2NRR'.

3. A compound according to claim 1 wherein Y is $NR_7$ wherein $R_7$ is hydrogen or $C_{1-3}$ alkyl.

4. A compound according to claim 1 wherein Y is $CR_8R_9$ wherein $R_8$, $R_9$ each are independently H, or $C_{1-3}$ alkyl.

5. A compound according to claim 1 wherein each X is $CR_6$ and Y is $NR_7$ wherein each $R_6$ is independently selected from H, $C_{1-3}$ alkyl, and halo; and $R_7$ is hydrogen or $C_{1-3}$ alkyl.

6. A compound according to claim 1 wherein said compound is selected from the group consisting of:
N-[2-[4-(4-Chloro-2-fluorophenyl)-1-piperazinyl]phenyl]-4-methylbenzenesulfonamide (1),
N-[2-[4-(4-Chloro-2-fluorophenyl)-1-piperazinyl]phenyl]-N,4-dimethylbenzenesulfonamide (2),
N-[2-[4-(4-Chloro-2-fluorophenyl)-1-piperazinyl]phenyl]-4-(trifluoromethyl)benzenesulfonamide (3),
N-[2-[4-(4-Chloro-2-fluorophenyl)-1-piperazinyl]-3-pyridyl]-4-methylbenzenesulfonamide (4),
N-[4-[4-(4-Chloro-2-fluorophenyl)-1-piperazinyl]-5-pyrimidyl]-4-methylbenzenesulfonamide (5),
1-(4-Chloro-2-fluorophenyl)-4-[2-(tosylmethyl)phenyl]piperazine (6),
1-(4-Chloro-2-fluorophenyl)-4-[2-(1-tosylethyl)phenyl]piperazine (7),
N1-[2-[4-(4-Chloro-2-fluorophenyl)-1-piperazinyl]phenyl]-N4,N4-dimethylbenzene-1,4-disulfonamide (8),
N1-[2-[4-(3-Methoxyphenyl)-1-piperazinyl]phenyl]-N4,N4-dimethylbenzene-1,4-disulfonamide (9),
N1-[2-[4-(2-Methoxyphenyl)-1-piperazinyl]phenyl]-N4,N4-dimethylbenzene-1,4-disulfonamide (10),
N1,N1-Dimethyl-N4-[2-(4-phenyl-1-piperazinyl)phenyl]benzene-1,4-disulfonamide (11),
N-[2-[4-(4-Chloro-2-fluorophenyl)-1-piperazinyl]phenyl]-4-(difluoromethyl)benzenesulfonamide (12), N-[2-[4-(4-Chloro-2-fluorophenyl)-2-methyl-1-piperazinyl]phenyl]-4-methylbenzenesulfonamide (13), N-[2-[4-(4-Chloro-2-fluorophenyl)-1-piperazinyl] phenyl]-4-methoxybenzenesulfonamide (14), N-[2-[4-(4-Chloro-2-fluorophenyl)-1-piperazinyl]phenyl]-2-methylbenzenesulfonamide (15), N-[2-[4-(4-Chlorophenyl)-1-piperazinyl]phenyl]-4-methylbenzenesulfonamide (16), 4-Methyl-N-[2-[4-(p-tolyl)-1-piperazinyl] phenyl] benzenesulfonamide (17), N-[2-[4-(4-Methoxyphenyl)-1-piperazinyl]phenyl]-4-methylbenzenesulfonamide (18), and N-[2-[4-(4-Chloro-2-fluorophenyl)-1-piperazinyl] phenyl]-4-cyanobenzenesulfonamide (19).

7. A method of treating a disease in a subject comprising administering to the subject a compound of claim 1.

8. A method of treating a disease in a subject comprising administering to the subject a composition comprising a compound of claim 1.

9. The method of claim 8, wherein the disease is mediated by loss-of-function in TRPML1, including ML4 and NPC.

10. The method of claim 8, wherein the disease is a lysosome storage disease.

11. The method of claim 8, wherein the disease is an age-related neurodegenerative disease, including Alzheimer's Disease, Parkinson's Disease, and Huntington's Disease.

12. The method of claim 8, wherein the disease or disease symptom is Muscular Dystrophy.

13. The method of claim 8, wherein the disease or disease symptom is related to oxidative stress or reactive oxygen species (ROS).

14. A method of using a compound of claim 1, or a composition comprising a compound of claim 1, as an anti-aging agent.

15. A method of treating oxidative stress or reactive oxygen species (ROS) related diseases or disease symptoms comprising administering an effective amount of a TRPML1 agonist or a composition comprising of a TRPML1 agonist to a subject with such a disease.

16. A method of using a TRPML1 agonist as an anti-ageing agent.

17. The method of claim 16, wherein a TRPML1 agonist or a composition comprising of a TRPML1 agonist is administered to a subject for the treatment of skin ageing.

18. The method of claim 16, wherein a TRPML1 agonist or a composition comprising of a TRPML1 agonist is administered to a subject for the treatment of photo ageing.

* * * * *